(12) United States Patent
Heneveld

(10) Patent No.: US 11,648,003 B2
(45) Date of Patent: May 16, 2023

(54) BIOLOGICAL TISSUE ACCESS AND CLOSURE APPARATUS, SYSTEMS AND METHODS

(71) Applicant: Suture Ease, Inc., San Jose, CA (US)

(72) Inventor: Scott Heneveld, Whitmore, CA (US)

(73) Assignee: Suture Ease, Inc., San Jose, CA (US)

( * ) Notice: Subject to any disclaimer, the term of this patent is extended or adjusted under 35 U.S.C. 154(b) by 127 days.

(21) Appl. No.: 17/484,265

(22) Filed: Sep. 24, 2021

(65) Prior Publication Data
US 2022/0008064 A1    Jan. 13, 2022

Related U.S. Application Data

(60) Division of application No. 16/418,463, filed on May 21, 2019, now Pat. No. 11,154,294, which is a continuation-in-part of application No. 15/991,441, filed on May 29, 2018, now Pat. No. 10,702,263.

(60) Provisional application No. 62/655,151, filed on Apr. 9, 2018, provisional application No. 62/618,634, filed on Jan. 18, 2018, provisional application No. 62/512,180, filed on May 30, 2017.

(51) Int. Cl.
*A61B 17/04* (2006.01)
*A61B 17/34* (2006.01)

(52) U.S. Cl.
CPC ...... *A61B 17/0469* (2013.01); *A61B 17/0482* (2013.01); *A61B 17/0491* (2013.01); *A61B 17/3423* (2013.01); *A61B 2017/3447* (2013.01)

(58) Field of Classification Search
CPC ............ A61B 17/0469; A61B 17/0482; A61B 17/0491; A61B 17/3423; A61B 2017/3447
See application file for complete search history.

(56) References Cited

U.S. PATENT DOCUMENTS

| | | | | |
|---|---|---|---|---|
| 5,713,870 A | * | 2/1998 | Yoon | A61B 17/3496 606/198 |
| 6,451,031 B1 | * | 9/2002 | Kontos | A61B 90/92 606/144 |
| 7,063,710 B2 | * | 6/2006 | Takamoto | A61B 17/0469 606/139 |
| 7,235,087 B2 | * | 6/2007 | Modesitt | A61B 17/0483 606/144 |

(Continued)

*Primary Examiner* — Phong Son H Dang
(74) *Attorney, Agent, or Firm* — Francis Law Group

(57) ABSTRACT

A method for closing an opening in biological tissue of intra-abdominal structures, which includes the steps of (i) providing a tissue closure system that includes a suture guide sub-system for engaging tissue disposed proximate the tissue opening and a suture passer sub-system that slideably engages the suture guide sub-system, (ii) inserting the suture guide sub-system into and through a tissue opening, (iii) inserting the suture passer sub-system with a section of suture engaged thereto into and through a first tissue region, (iv) rotating the suture guide sub-system, (v) inserting the suture passer sub-system with another section of suture engaged thereto into and through a second tissue region, (vi) withdrawing suture guide sub-system, (vii) releasing both sections of the suture captured by the suture guide sub-system, and (viii) drawing both sections of the suture together, wherein the first and second tissue regions are drawn together and the tissue opening is closed.

3 Claims, 32 Drawing Sheets

(56) References Cited

U.S. PATENT DOCUMENTS

| | | | |
|---|---|---|---|
| 8,267,947 B2 * | 9/2012 | Pantages | A61B 17/0487 |
| | | | 606/144 |
| 9,155,533 B2 * | 10/2015 | Henrichsen | A61B 17/0482 |
| 9,386,980 B2 * | 7/2016 | Smith | A61B 17/0491 |
| 9,999,419 B2 * | 6/2018 | Bachman | A61B 17/0401 |
| 10,383,620 B2 * | 8/2019 | Harrison | A61B 17/0469 |
| 2002/0198542 A1 * | 12/2002 | Yamamoto | A61B 17/0469 |
| | | | 606/144 |
| 2005/0149065 A1 * | 7/2005 | Modesitt | A61B 17/0057 |
| | | | 606/144 |
| 2005/0154403 A1 * | 7/2005 | Sauer | A61B 17/0469 |
| | | | 606/139 |
| 2006/0069397 A1 * | 3/2006 | Nobles | A61B 17/0057 |
| | | | 606/144 |
| 2007/0032799 A1 * | 2/2007 | Pantages | A61B 17/0487 |
| | | | 606/144 |
| 2008/0045976 A1 * | 2/2008 | Gibbons | A61B 17/0469 |
| | | | 606/139 |
| 2008/0045979 A1 * | 2/2008 | Ma | A61B 17/0482 |
| | | | 606/144 |
| 2009/0222027 A1 * | 9/2009 | Sauer | A61B 17/06061 |
| | | | 606/144 |
| 2010/0331623 A1 * | 12/2010 | Sauer | A61B 1/0014 |
| | | | 606/139 |
| 2013/0190781 A1 * | 7/2013 | Fortson | A61B 17/0057 |
| | | | 606/144 |

\* cited by examiner

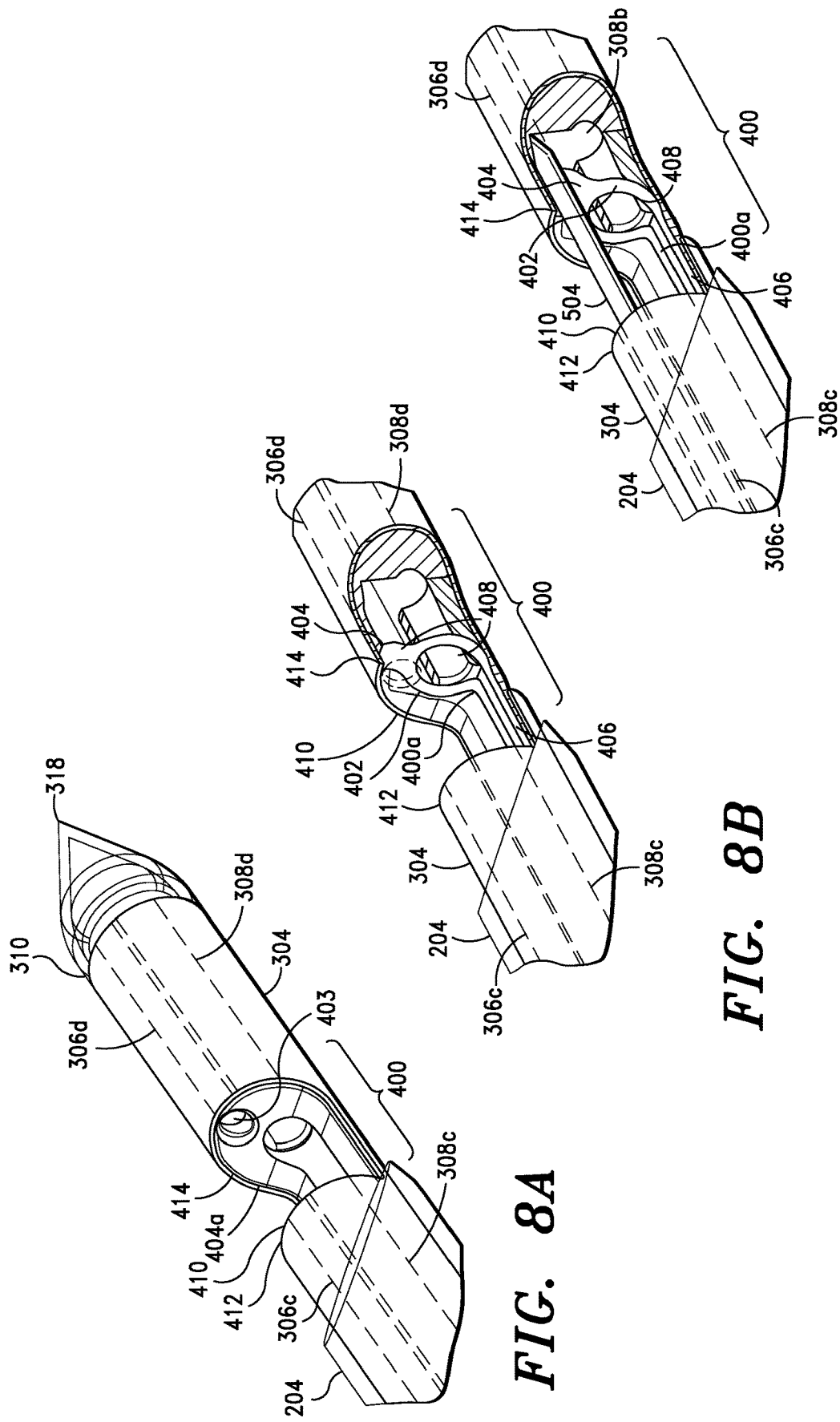

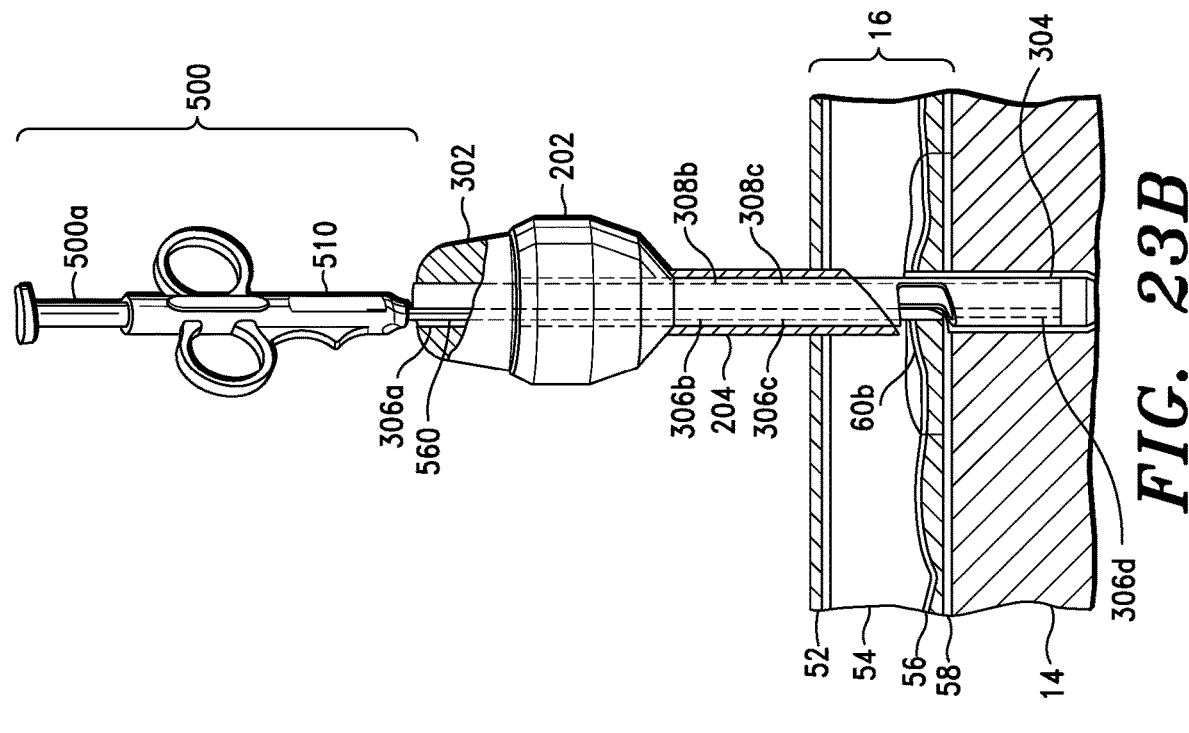
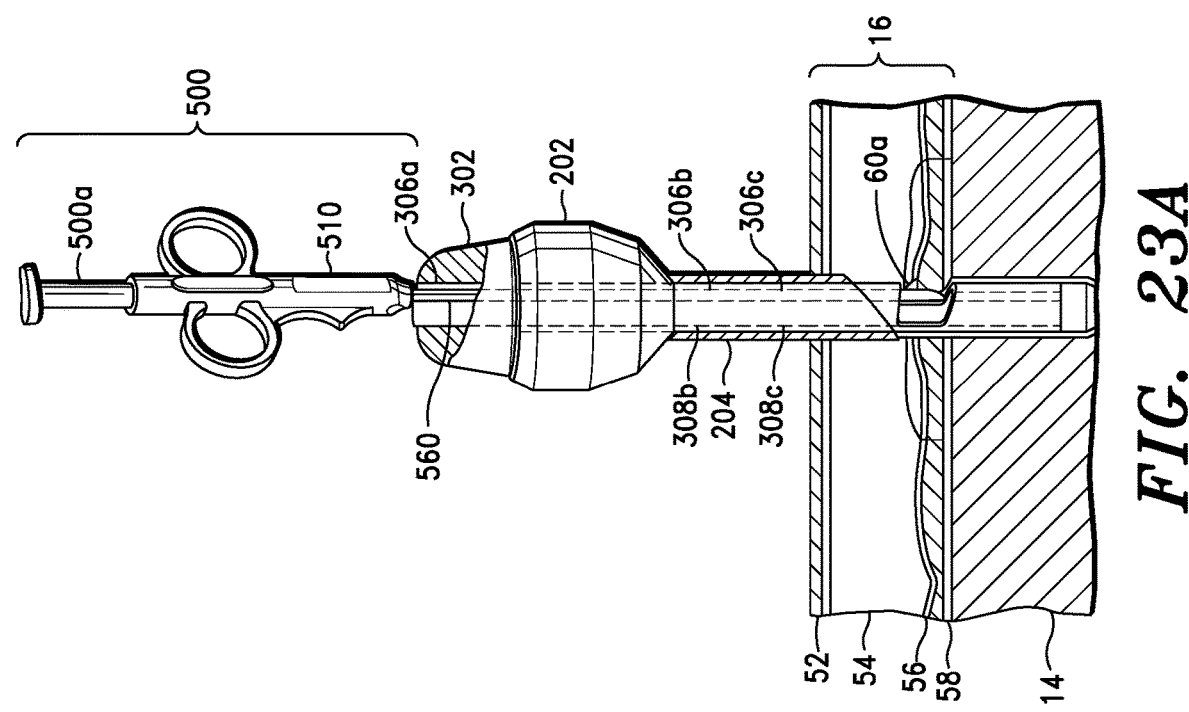

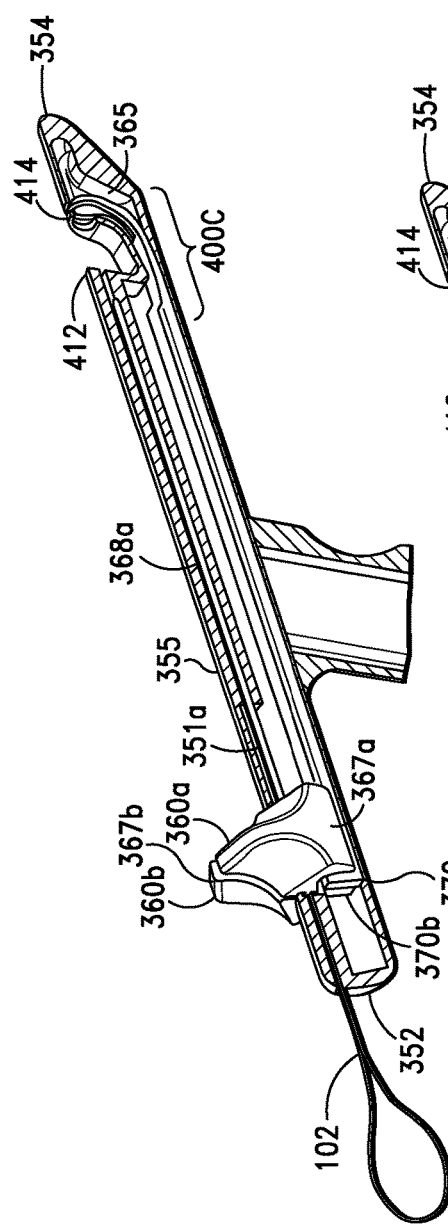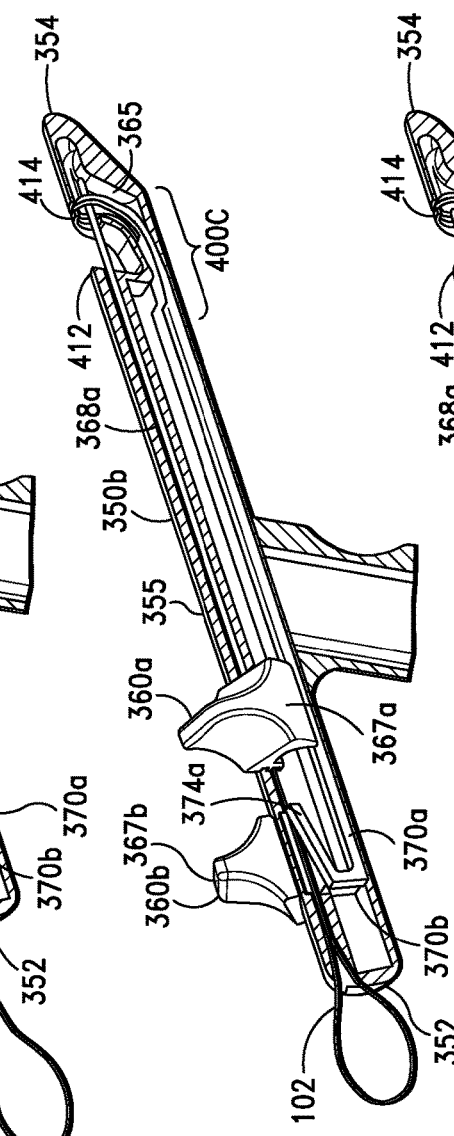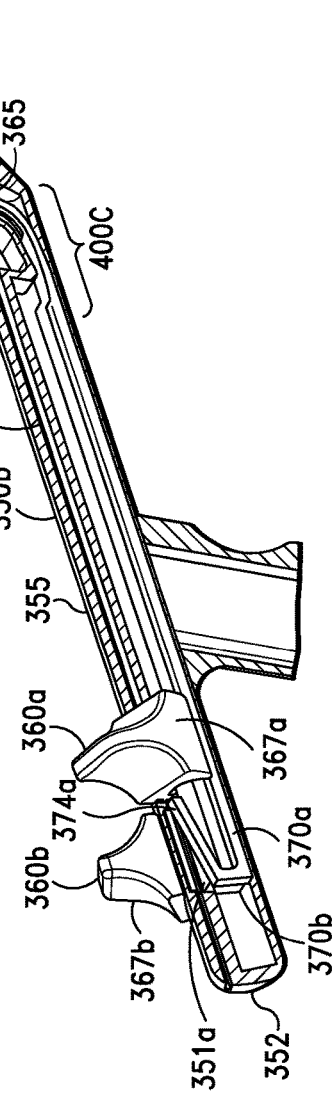
FIG. 29A
FIG. 29B
FIG. 29C

BIOLOGICAL TISSUE ACCESS AND CLOSURE APPARATUS, SYSTEMS AND METHODS

CROSS-REFERENCES TO RELATED APPLICATIONS

This application is a division of U.S. application Ser. No. 16/418,463, filed on May 21, 2019, which is a continuation-in-part of U.S. application Ser. No. 15/991,441, now U.S. Pat. No. 10,702,263, filed on May 29, 2018, which claims the benefit of U.S. Provisional Application No. 62/512,180, filed on May 30, 2017, U.S. Provisional Application No. 62/618,634, filed on Jan. 18, 2018, and U.S. Provisional Application No. 62/655,151, filed on Apr. 9, 2018.

FIELD OF THE INVENTION

The present invention relates to apparatus, systems and methods for accessing internal structures and closing biological tissue. More particularly, the present invention relates to apparatus, systems and methods for accessing internal structures; particularly, intra-abdominal structures, and approximation, ligation, fixation and closure of openings in biological tissue; particularly, laparoscopic ports or incisions in biological tissue.

BACKGROUND OF THE INVENTION

As reported in a Jan. 31, 2017 iData Research press release, approximately 3.5 million laparoscopic surgical procedures are performed each year in the U.S and more than 7.5 million worldwide. The most common laparoscopic surgical procedures include a cholecystectomy, appendectomy, gastric bypass, nephrectomy and hernia repair.

As illustrated in FIG. 1, a laparoscopic surgical procedure generally comprises insertion of a trocar/cannula system 10, such as shown in FIGS. 2-4, through layers of body tissue, such as the tissue 16 of an abdominal wall 12, to a desired position proximate an internal organ of interest, such as the gallbladder.

As illustrated in FIG. 2-4, the conventional trocar/cannula system 10 comprises two seminal components: (i) a central obturator 20, which comprises a handle 22, shaft 23 and a puncturing tip 24, and a cannula port 26. The puncturing tip 24 is configured pierce through tissue and provide an incision for insertion of the cannula port 26. As discussed below, the cannula port 26 is configured to receive surgical instruments, e.g., endoscopes, and the like, therein, and, hence, facilitate surgical procedures to be performed inside a body cavity, such as an abdomen cavity 14.

After the puncturing tip 24 and, hence, obturator 20 are disposed in a desired position within the body cavity, the obturator 20 is removed from the cannula port 26. The cannula port 26 then provides an access or working portal through the tissue for surgical instruments to perform a desired surgical procedure inside the body cavity, e.g., a gastric bypass.

As is well known in the art, numerous laparoscopy methods currently exist for performing laparoscopic surgical procedures. One of the more commonly used laparoscopy methods is known as closed laparoscopy. Referring back to FIG. 1, closed laparoscopy employs a sharp needle (e.g., Veress™ needle) to pierce through tissue, such as abdominal wall tissue 16, and insufflate the body cavity, e.g., abdominal cavity 14, with an inert gas, such as carbon dioxide ($CO_2$). The process of insufflating the body cavity separates the cavity tissue and associated structure, e.g., abdominal wall 12, from the underlying organ(s), thus, creating a space or gap 18 for a surgeon to work within. A trocar/cannula system is then employed to maintain the insufflated space or cavity 18 and provide a working portal through which surgical instruments can be passed into and out of the insufflated cavity 18 to perform a desired surgical procedure.

As is also well known in the art, one of the most common post-operative complication associated with a laparoscopic surgical procedure is the incidence of trocar-site hernias, where a portion of an organ or fatty tissue protrudes through the opening in the tissue created by a trocar access portal. It is believed that inadequate closure of the trocar access portal is the primary cause of trocar-site hernias.

Various methods for closing a trocar access portal have thus been developed and employed. Although the noted methods can, in most instances, be employed to successfully close a trocar access portal, there are several significant drawbacks and disadvantages associated with the methods. Indeed, as discussed below, most, if not all, current trocar access portal closing methods are typically difficult to perform, require considerable time to execute and do not provide for a simple, reproducible and reliable means of closing the trocar access portal. Illustrative are the trocar access portal closing methods disclosed in U.S. Pat. Nos. 919,138, 3,946,740, 4,621,640, 8,109,943, and Pub. No. 2016/0228107.

U.S. Pat. Nos. 919,138, 3,946,740 and 4,621,640 disclose similar conventional methods for closing trocar access portals that comprise guiding a suture engaged to a needle through the trasversalis fascia with needle-nosed forceps or other specialized apparatus. A major drawback and disadvantage associated with the disclosed methods is that the apparatus and methods are primarily dependent on the dexterity of the surgeon operating the apparatus and executing the associated methods.

A further disadvantage associated with the methods disclosed in U.S. Pat. Nos. 919,138, 3,946,740 and 4,621,640 is that the surgeon operating the apparatus associated with the methods must either perform the trocar access portal closure "blind", i.e., without visual access to interior body tissues, e.g., intra-abdominal fascia, or with the assistance of an endoscope inserted into the body cavity from an additional access portal.

A further disadvantage is that an exposed needle must be handled by a surgeon inside of a body cavity with limited visual access, thus, which increases the risk of injury to the local structures inside of a patient, e.g., organs.

A further disadvantage associated with the apparatus and methods disclosed in U.S. Pat. No. 919,138, 3,946,740 and 4,621,640 is that, if the surgeon desires to place more than one suture throw through the tissue, the surgeon must reload the needle into a needle driver apparatus. This can be done extracorporeally, i.e., outside the body, in a manner similar to the initial loading of the suture device, or it can be done intracorporeally, i.e., inside the body. This process is time consuming and oftentimes a frustrating exercise in hand-to-eye coordination. The apparatus and methods are thus configured and, hence, primarily employed for use in open surgical procedures where there is room for the surgeon to manipulate the instrument(s).

Another drawback associated with the apparatus and associated methods disclosed in U.S. Pat. Nos. 919,138, 3,946,740 and 4,621,640 is that the apparatus can, and often times will, fail to effectively close tissue that is disposed proximate the trocar access portal, which greatly increases the patients risk of trocar-site herniation at the closure site.

The seminal complications associated with trocar-site herniation include organ necrosis and closed loop intestinal obstruction, which can be life-threating.

A further drawback is that patients with relatively thick body tissues increase the difficulty, time and risk of trocar access portal closure complications, such as a misplaced suture and/or penetration of a patient's organs with the suture needle.

U.S. Pat. No. 8,109,943 and Pub. No. 2016/0228107 disclose further apparatus and methods for closing trocar access portals. The disclosed apparatus generally comprises a trocar device that is loaded with operator actuated injectors. The injectors are configured and positioned to insert suture anchors with sutures attached thereto into the tissue of a patient, such as an abdominal wall.

A major drawback and disadvantage associated with the methods disclosed in U.S. Pat. No. 8,109,943 and Pub. No. 2016/0228107 is that the stitch produced does not encompass the anterior fascia and peritoneum and, hence, does not fully close the defect in a traditional manner. The efficacy of closing only the anterior fascia is often questioned by surgeons.

Further, the surgeon operating the trocar must again either perform the trocar access portal closure "blind", i.e., with limited visual access to interior body tissues, or with the assistance of an endoscope inserted into the body cavity from an additional access portal.

A further drawback associated with the methods disclosed in U.S. Pat. No. 8,109,943 and Pub. No. 2016/0228107 is that, even if the trocar device is appropriately positioned in a patient, there is no means to ensure that the anchors will completely penetrate the targeted body tissues and successfully close the trocar access portal.

A further drawback is that at least two (2) exposed suture needles must be handled by a surgeon inside of a patient's body cavity with limited visual aid, which, as indicated above, greatly increases the risk of injury to the local structures, e.g., organs.

Another drawback associated with the apparatus and methods disclosed in U.S. Pat. No. 8,109,943 and Pub. No. 2016/0228107 is that the suture anchors are formed from polymeric and/or metallic materials, i.e., non-endogenous material structures, which, after the laparoscopic procedure, remain anchored in the body tissue of the patient. The suture anchors thus can, and often times will, elicit an adverse inflammatory response in the patient. There is also a substantial risk of dislodgment of the suture anchors from body tissue, which can also cause serious postoperative complications.

A further method for closing a trocar access portal comprises use of a trocar device manufactured and distributed by Medtronic® under the tradename VersaOne™ All-in-One (AIO) trocar and closure device.

The Medtronic® device, which is illustrated in FIGS. 2-4, employs a guide component that is configured to be positioned in the trocar cannula. The guide component includes two (2) diagonally oriented channels that are configured to guide a suture through two (2) contra-laterally opposed regions of body tissue, e.g., intra-abdominal fascia. The suture is guided through the two (2) contra-laterally opposed regions of body tissue using a specialized grasper needle that can traverse the diagonally oriented channels and a secondary grasper tool controlled from an additional trocar access portal that is disposed proximate the trocar device.

Several drawbacks and disadvantages are similarly associated with the Medtronic® device and associated method. A major drawback and disadvantage is that there is no reliable means associated with the Medtronic® device for a surgeon to assess whether the device is properly positioned in (or through) the body tissue of a patient. The device merely employs fixed circumferential bands on the device housing to indicate and, hence, ensure desired tissue approximation positioning. It is, however, very difficult, if not impossible to achieve proper trocar device positioning for every patient via the fixed circumferential bands due to varying body tissue thicknesses encountered from patient-to-patient. As a result of inaccurate positioning of the Medtronic® device, the associated method can cause unintended damage or trauma to local tissues. The Medtronic® method can also fail to successfully close a trocar access portal, which can lead to the above noted complications, e.g., trocar-site herniation.

A further drawback associated with the Medtronic® method is that the method requires a secondary grasper tool controlled from an additional trocar access portal in order to guide a suture through the two (2) contra-laterally opposed regions of body tissue. A surgeon is thus required to induce further tissue trauma by deploying a second trocar in a patient's body tissue to generate an additional trocar access portal for the grasper tool.

A further drawback associated with the Medtronic® method is that it is extremely difficult and cumbersome to manipulate and engage the intra-cavity suture with the grasper tool.

Another drawback associated with the Medtronic® method is that the method also requires that at least one (1) sharp instrument be introduced to and manipulated within a body cavity with limited visual access to interior body tissues, which as indicated above, substantially increases the risk of injury to the local structures inside of a patient, e.g., organs.

It is thus desirable to provide an improved tissue closure system and method that substantially reduces or eliminates the disadvantages and drawbacks associated with conventional, known tissue closure and associated methods.

It is therefore an object of the present invention to provide tissue closure systems and associated methods that substantially reduce or eliminate the disadvantages and drawbacks associated with conventional, known tissue closure apparatus and associated methods.

It is a further object of the present invention to provide tissue access and closure systems that can be readily employed to facilitate various laparoscopic surgical procedures in a simple and economical manner.

It is a further object of the present invention to provide tissue access and closure systems that can be readily employed to access internal structures; particularly, intra-abdominal structures in a minimally invasive manner.

It is a further object of the present invention to provide tissue access and closure systems that can be readily employed to effectively approximate, ligate, fixate and close biological tissue; particularly, laparoscopic ports or incisions in biological tissue.

SUMMARY OF THE INVENTION

The present invention is directed to apparatus, systems and methods that are configured to (i) pierce through tissue and provide access to internal structures; particularly, intra-abdominal structures, and (ii) close openings in biological tissue, more preferably, approximate and/or ligate and/or fixate and close openings in biological tissue; particularly, laparoscopic ports or incisions in biological tissue.

In one embodiment of the invention there is thus provided a method for closing an opening in biological tissue, comprising the steps of:

(i) providing a tissue closure system comprising a suture guide sub-system and suture passer sub-system, the suture guide sub-system comprising an elongated housing comprising a distal region and an open internal region disposed in the distal region, the distal region being configured to transition into and through a tissue structure, the suture guide sub-system housing further comprising a suture passer lumen that is sized and configured to receive the suture passer sub-system therein and an open tissue positioning region proximate a distal region of the suture guide sub-system housing that is adapted to receive tissue therein, the suture guide sub-system housing further comprising adjustable tissue capture means disposed proximate the open tissue positioning region that is configured and positioned to linearly translate from a first guide shaft position to a second guide shaft position, wherein the adjustable tissue capture means is capable of engaging tissue disposed in the open tissue positioning region, the distal region of the suture guide sub-system housing further comprising suture engagement means comprising a suture capture door that is configured to obstruct passage of the suture passer sub-system through the suture guide sub-system housing when in a closed position, the suture capture door is further configured to transition from the closed position to an open position, wherein passage of the suture passer sub-system through the suture guide sub-system housing is allowed, the suture capture door is further configured to engage and retain a suture that is releasably secured to the suture passer sub-system when the suture passer sub-system and engaged suture are inserted through and subsequently withdrawn from the suture capture door, the suture passer sub-system comprising an actuator, a suture passer cannula and a suture deployment shaft, the suture passer cannula being configured to slidably receive the suture deployment shaft therein, the suture deployment shaft comprising suture deployment and capture means for delivering a suture to biological tissue and capturing and releasably securing the suture therewith;

(ii) inserting the suture guide sub-system into and through a tissue opening in a biological tissue structure;

(iii) positioning the open tissue positioning region of the suture guide sub-system proximate a first tissue region of the biological structure, wherein the first tissue region is disposed in the open tissue positioning region of the suture guide sub-system;

(iv) engaging a first section of a suture with the suture passer sub-system;

(v) inserting the suture passer sub-system and the engaged first section of the suture into the suture guide sub-system, wherein the suture passer cannula is disposed proximate the first tissue region of the biological structure;

(vi) inserting the suture passer cannula of the suture passer sub-system and the engaged first section of the suture into and through the first tissue region of the biological structure and through the suture capture door of the suture guide sub-system;

(vii) withdrawing the suture passer cannula through the suture capture door and out of the first tissue region of the biological structure, wherein the first section of the suture is ensnared by the suture capture door and routed through the first tissue region of the biological structure;

(viii) withdrawing the suture passer sub-system out of the suture guide sub-system;

(ix) rotating the suture guide sub-system circumferentially, wherein a contralateral second tissue region of the biological structure is disposed in the open tissue positioning region of the suture guide sub-system;

(x) engaging a second section of the suture with the suture passer sub-system;

(xi) inserting the suture passer sub-system and engaged second section of the suture into and through the second tissue region of the biological structure and through the suture capture door of the suture guide sub-system;

(xii) withdrawing the first suture passer cannula through the suture capture door and out of the second tissue region of the biological structure, wherein the second section of the suture is ensnared by the suture capture door and routed through the second tissue region of the biological structure;

(xiii) withdrawing the suture passer sub-system out of the suture guide sub-system;

(xiv) withdrawing the suture guide sub-system from the first biological structure;

(xv) releasing the first and second sections of the suture that is ensnared by the suture capture door; and (xvi) drawing the first and second sections of the suture together, wherein first and second tissue regions of the biological structure are drawn together and, thereby, the tissue opening in the biological tissue structure is closed.

BRIEF DESCRIPTION OF THE DRAWINGS

Further features and advantages will become apparent from the following and ma particular description of the preferred embodiments of the invention, as illustrated in the accompanying drawings, and in which like referenced characters generally refer to the same parts or elements throughout the views, and in which:

FIGS. 5A-5C are partial perspective views of the suture guide sub-system shown in FIG. 7A, illustrating one embodiment of a tissue positioning sub-system, according to the invention;

FIGS. 23A and 23B are front plan views of the assembled cannula, suture guide and suture passer sub-systems shown in FIGS. 5, 6 and 7, illustrating the engagement of biological tissue with a tissue positioning sub-system, according to the invention;

FIG. 29A is a partial perspective view of the tissue closure system shown in FIG. 25 with an actuator in a fully retracted position, according to the invention;

FIG. 29B is another partial perspective view of the tissue closure system shown in FIG. 25 with the actuator shown in FIG. 29A in an advanced position, according to the invention;

FIG. 29C is another partial perspective view of the tissue closure system shown in FIG. 25 with the actuator shown in FIG. 29A in a partially retracted position, according to the invention;

DETAILED DESCRIPTION OF THE PREFERRED EMBODIMENT

Figure 1:
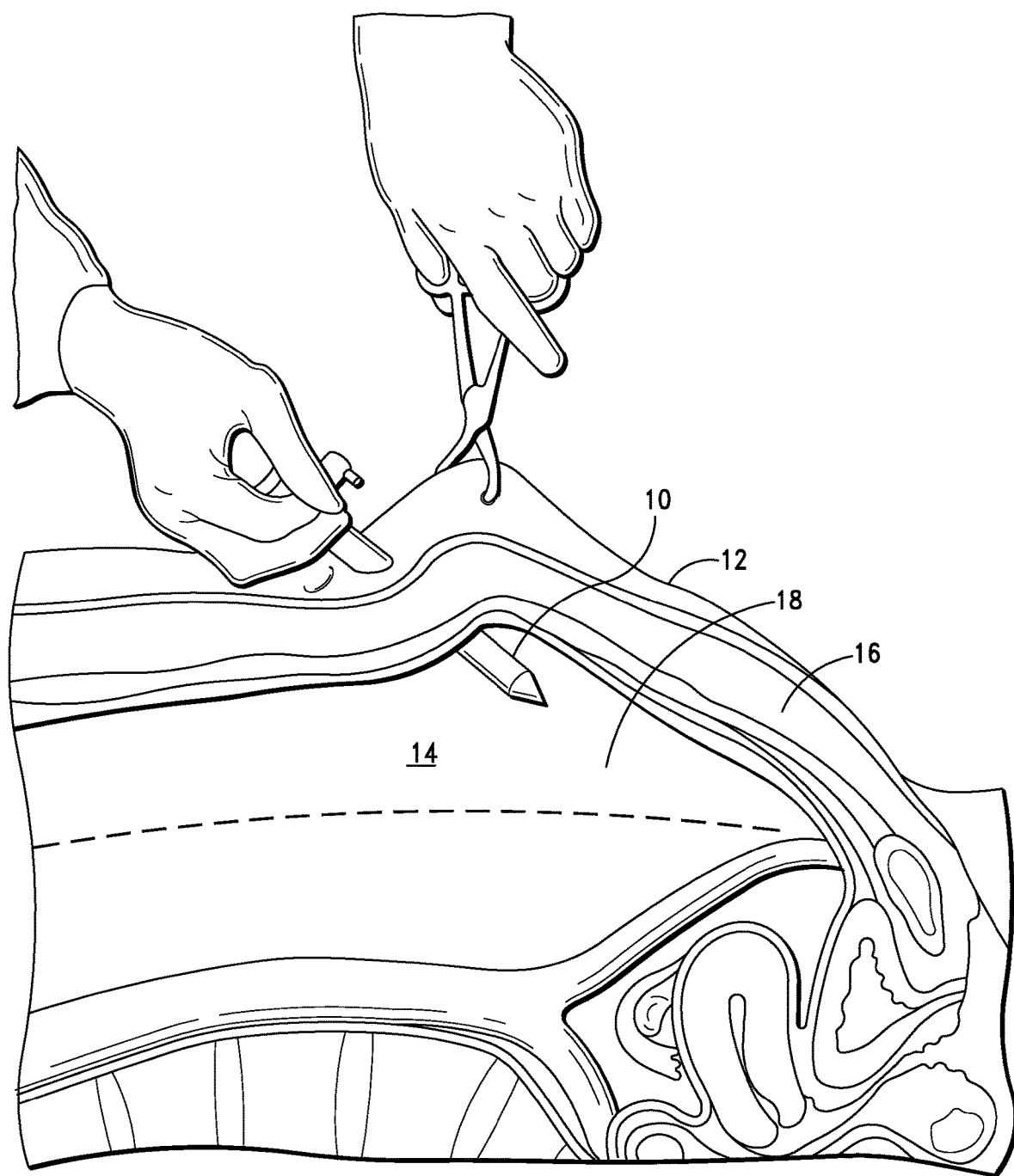
FIG. 1 is an illustration of a prior art laparoscopic surgical procedure employing a conventional trocar apparatus.
Figure 2:
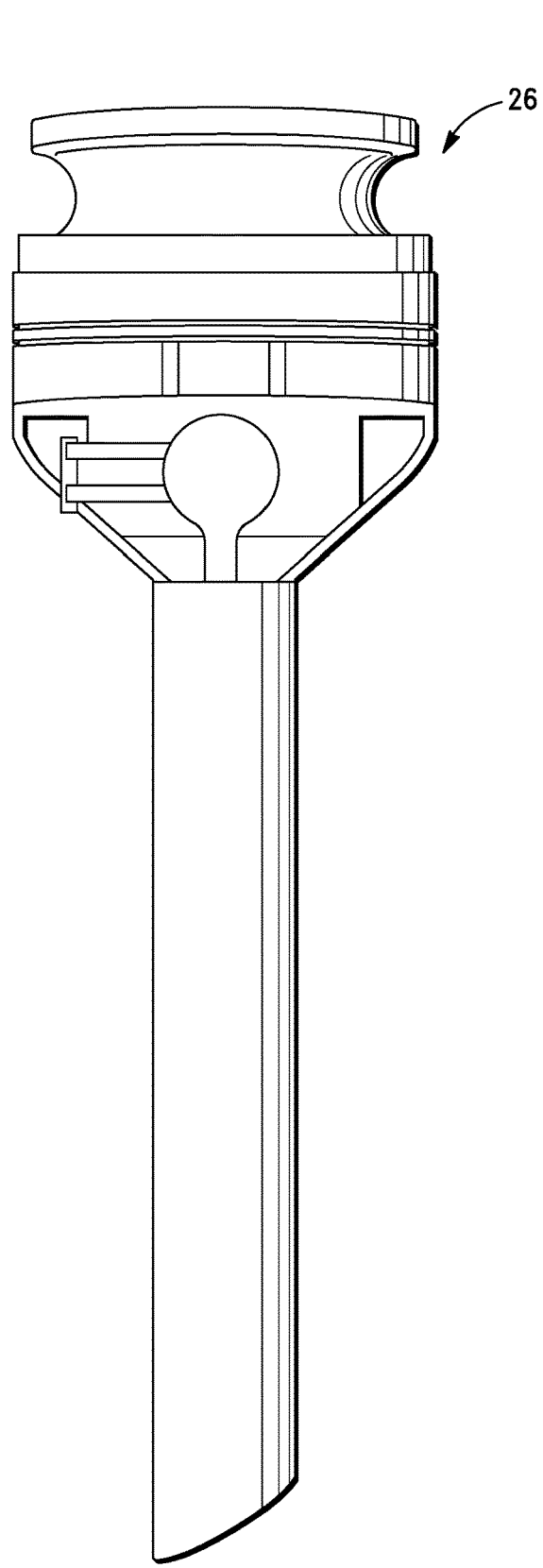
FIG. 2 is a front plan view of a prior art cannula port.
Figure 3:
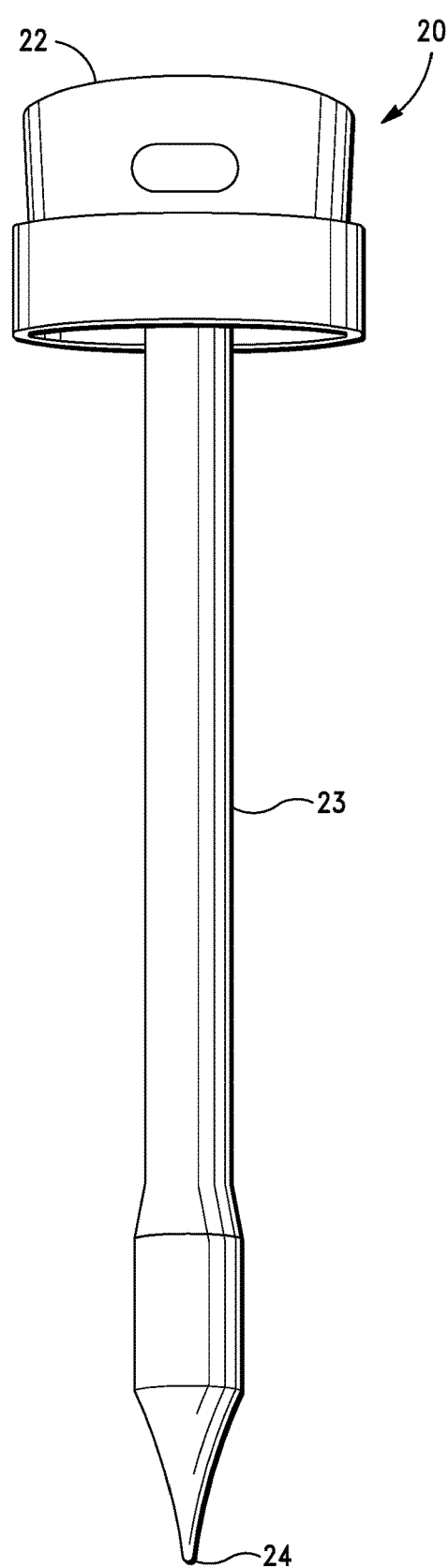
FIG. 3 is a front plan view of a prior art obturator that is configured to cooperate with the cannula port shown in FIG. 2.
Figure 4:
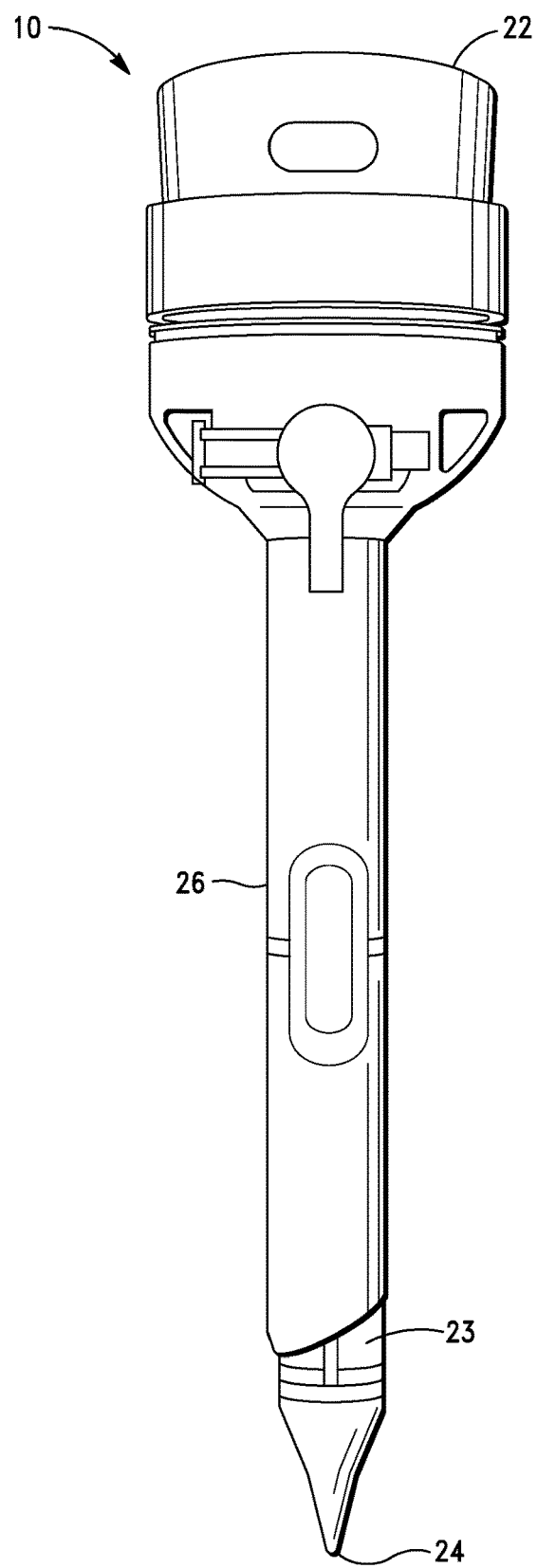
FIG. 4 is a front plan view of a prior art trocar assembly comprising the cannula port and obturator shown in FIGS. 2 and 3.

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that, although the present invention is described and illustrated in connection with laparoscopic procedures, the invention is not limited to such procedures. According to the invention, the apparatus, systems and methods of the invention can also be employed in connection with a multitude of other surgical procedures, including, without limitation, patent foramen ovale (PFO) closure, left ventricular closure and vascular, i.e., artery and vein, closure.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a, "an" and "the" include plural referents unless the content clearly dictates otherwise. Thus, for example, reference to "an incision" includes two or more incisions and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

DEFINITIONS

The terms "tissue" and "biological tissue" are used interchangeably herein, and mean and include mammalian biological tissue, such as, by way of example, human abdominal tissue.

The term "biological cavity", as used herein, means and includes any cavity or space in a mammalian tissue structure.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "one configuration," "one embodiment," "one aspect," and "a configuration," "an embodiment" and "an aspect," as used herein, means that a particular feature, structure, or characteristic described in connection with the configuration may be included in at least one configuration and not that any particular configuration is required to have a particular feature, structure or characteristic described herein unless set forth in the claim.

The phrase "in one configuration" or similar phrases employed herein do not necessarily refer to the same configuration and, unless specifically stated, do not limit the inclusion of a particular element of the invention to a single configuration. The element may thus be included in other or all configurations discussed herein.

The term "substantially", as used herein, means and includes the complete or nearly complete extent or degree of an action, characteristic, property, state, structure, item, or result to function as indicated. For example, an object that is "substantially" enclosed would mean that the object is either completely enclosed or nearly completely enclosed. The exact allowable degree of deviation from absolute completeness may in some cases depend on the specific context, such that enclosing nearly all of the length of a lumen would be substantially enclosed, even if the distal end of the structure enclosing the lumen had a slit or channel formed along a portion thereof.

Use of the term "substantially" is equally applicable when used in a negative connotation to refer to the complete or near complete lack of an action, characteristic, property, state, structure, item, or result. For example, structure which is "substantially free of" a bottom would either completely lack a bottom or so nearly completely lack a bottom that the effect would be effectively the same as if it completely lacked a bottom.

The term "comprise" and variations of the term, such as "comprising" and "comprises," means "including, but not limited to" and is not intended to exclude, for example, other components, elements or steps.

The following disclosure is provided to further explain in an enabling fashion the best modes of performing one or more embodiments of the present invention. The disclosure is further offered to enhance the understanding and appreciation for the inventive principles and advantages thereof, rather than to limit in any manner the invention. The invention is defined solely by the appended claims, including any amendments made during the pendency of this application, and all equivalents of those claims as issued.

As indicated above, the present disclosure is directed to tissue access and closure apparatus, systems and methods for accessing internal structures; particularly, intra-abdominal structures, and closing openings in biological tissue; particularly, laparoscopic ports or incisions in biological tissue.

In a preferred embodiment of the invention, the tissue access and closure ("TAC") systems are configured to (i) pierce through biological tissue and provide access to internal structures; particularly, intra-abdominal structures, and (ii) close openings in biological tissue, more preferably, approximate and/or ligate and/or fixate and close openings in biological tissue; particularly, laparoscopic ports or incisions in biological tissue.

As discussed in detail below, in a preferred embodiment of the invention, the TAC systems of the invention comprise the following sub-systems: (i) a cannula sub-system, (ii) suture guide sub-system, (ii) tissue positioning sub-system, and (iv) suture passer sub-system.

Figure 5:
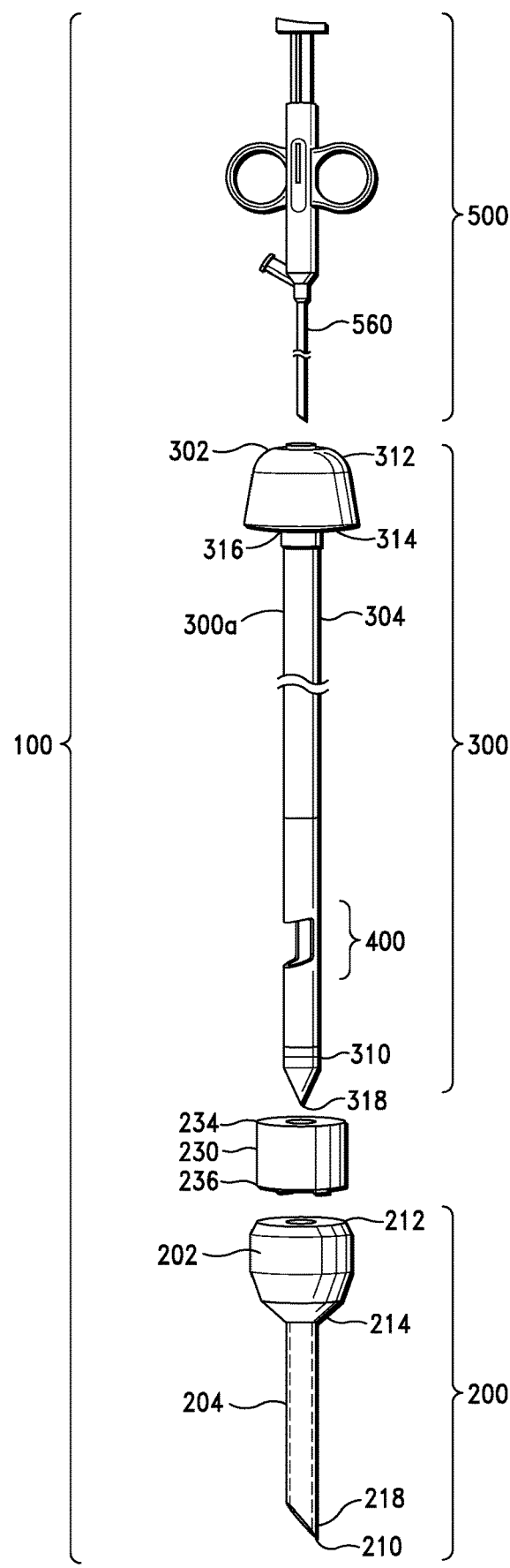
FIG. 5 is an exploded view of one embodiment of a tissue access and closure system, illustrating a cannula, suture guide and suture passer sub-system thereof according to the invention.

Referring now to FIG. 5, there is shown an exploded view of one embodiment of a TAC system (denoted "100") of the invention comprising a cannula sub-system 200, suture guide sub-system 300, tissue positioning subsystem 400, and suture passer sub-system 500.

Referring now to FIGS. 6-20, each of the noted sub-systems will now be described in detail.

Cannula Sub-System

Figure 6:
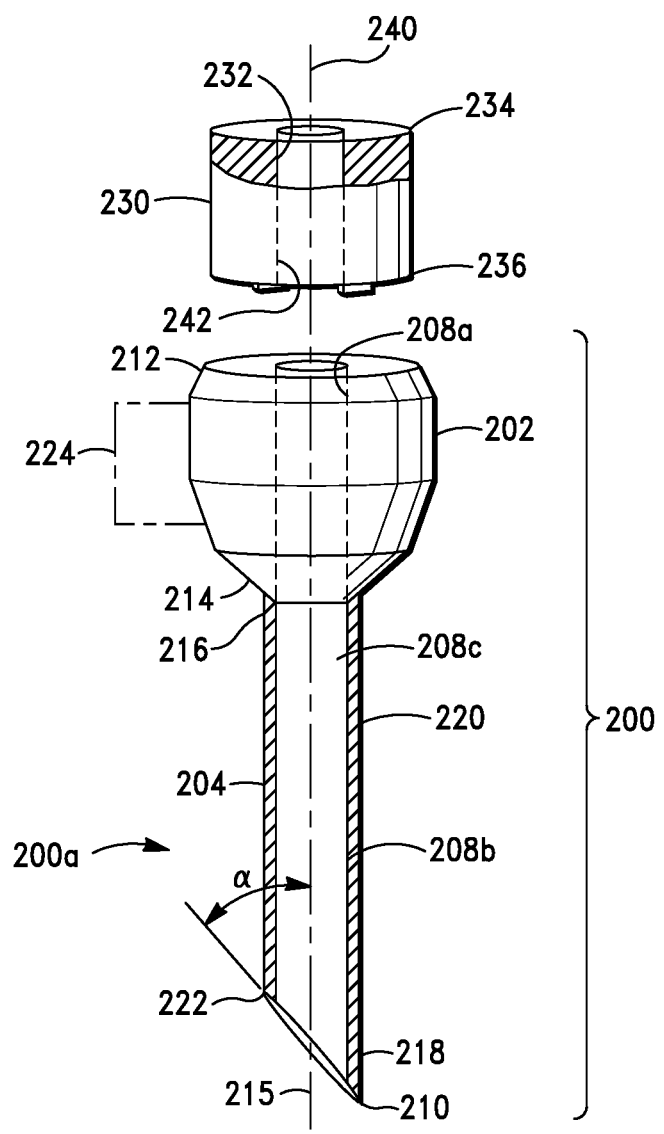
FIG. 6 is a front plan view of one embodiment of cannula sub-system, according to the invention.

Referring first to FIG. 6, there is shown one embodiment of a cannula sub-system 200a of the invention. As illustrated in FIG. 6, the cannula sub-system 200a comprises a cannula base member 202, comprising proximal and distal ends 212, 214, and a cannula shaft 204, which also comprises proximal and distal ends 216, 218. In a preferred embodiment, the cannula shaft proximal end 216 is in direct communication with, i.e., secured to, the base member distal end 214.

As further illustrated in FIG. 6, the cannula base member 202 includes a first cannula lumen 208a, which extends from the proximal end 212 to the distal end 214 of the base member 202, and the cannula shaft 204 includes a second cannula lumen 208b, which extends from the proximal end 216 to the distal end 218 of the cannula shaft 204.

In a preferred embodiment of the invention, the first and second cannula lumens 208a, 208b comprise the same diameter and are in an aligned relationship (forming a continuous, preferably, unobstructed cannula lumen 208c) when the cannula base member 202 is engaged to the cannula shaft 204, i.e., the cannula shaft proximal end 216 is in direct communication with, i.e., secured to, the base member distal end 214.

As discussed in detail below, the first and second cannula lumens 208a, 208b and, hence, continuous cannula lumen 208 are sized and configured to receive a suture guide sub-system 300 of the invention therein. According to the invention, the continuous cannula lumen 208c also defines an access port for surgical instruments that facilitates entry thereof into a body cavity when the cannula sub-system 200 is positioned therein.

In a preferred embodiment of the invention, the diameter of the first and second cannula lumens 208a, 208b and, hence, continuous cannula lumen 208c is in the range of 8-20 mm.

According to the invention, the cannula shaft distal end 210 can comprise various configurations, including, but not limited to, a beveled, curved and serrated edge, which is configured to pierce through biological tissue.

As illustrated in FIG. 6, in a preferred embodiment, the cannula shaft distal end 210 comprises a beveled edge having an angle "a" in the range of approximately 1-90° with respect to the longitudinal axis 215 of the cannula shaft 204. More preferably, the angle "d" of the beveled cannula end 210 is in the range of approximately 45°-90°.

According to the invention, the cannula shaft 204 can also comprise various conventional materials, including, but not limited to, metal and polymeric materials. Thus, in some embodiments, the cannula shaft 204 comprises stainless steel. In some embodiments, the cannula shaft 204 comprises a shape memory alloy, such as a nickel titanium alloy (Nitinol™).

In some embodiments, the cannula shaft 204 comprises a polymeric material. According to the invention, suitable polymeric materials comprise polyethylene, polyester, polypropylene, acrylic, polycarbonate, and like polymeric materials.

In some embodiments, the cannula shaft 204 comprises textured features on at least a portion of the cannula shaft exterior surface 220 to reduce the risk of accidental dislodgment of the cannula sub-system 200 from a biological tissue structure. According to the invention, suitable textured features include, but are not limited to, grooves and ribs.

According to the invention, the cannula shaft exterior surface 220 can also comprise an outer coating that facilitates or eases entry into and through body tissue or stabilizes the cannula shaft 204 when positioned in body tissue and/or a body cavity. Suitable coatings comprise, without limitation, polytetrafluoroethylene (FE) and parylene coatings.

According to the invention, the cannula shaft 204 can comprise various diameters and lengths. In some embodiments, the cannula shaft 204 comprises an outer diameter in the range of approximately 5-30 mm. More preferably, the outer diameter of the cannula shaft 204 is in the range of approximately 10-20 mm.

In some embodiments, the cannula shaft 204 comprises a length in the range of approximately 1-500 mm. More preferably, the length of the cannula shaft 204 is in the range of approximately 75-200 mm.

In some embodiments, the cannula shaft wall 222 comprises a thickness in the range of 1-10 mm. More preferably, the thickness of the cannula shaft wall 222 is in the range of approximately 0.25-4 mm.

In some embodiments of the invention, the cannula sub-system 200a is further configured to insufflate a cavity in a biological tissue structure, e.g., an intra-abdominal cavity. In the noted embodiments, the cannula subsystem 200a includes an insufflation sub-system 224 (shown in phantom) that is configured to receive an insufflation management system.

In some embodiments, the cannula insufflation sub-system 224 is configured to receive and operate in conjunction with a CONMED® AirSeal® iFS insufflation management system.

As illustrated in FIG. 6, in one embodiment of the invention, the cannula sub-system 200a includes a cannula spacer 230, which, as discussed in detail below, is configured to receive and position a suture guide sub-system 300 of the invention in a "tissue access configuration."

As further illustrated in FIG. 6, the cannular spacer 230 comprises an internal lumen 232 and proximal and distal ends 234, 236.

According to the invention, the cannula spacer 230 is preferably configured to engage the proximal end 212 of the cannula base member 202, wherein the longitudinal axis of the cannula spacer 230 (denoted "240") and longitudinal axis 215 of the cannula shaft 204 are coincident. More preferably, the spacer lumen 232 is in an aligned relationship with the cannula continuous lumen 208c when the cannula spacer 230 is engaged to the cannula base member 202.

As discussed in detail below, in a preferred embodiment, the cannula spacer lumen 232 and continuous cannula lumen 208c are sized and configured to receive a guide sub-system 300 of the invention therein.

In some embodiments, the spacer lumen wall 242 comprises at least one continuous groove or notch (not shown) that is in a parallel relationship with longitudinal axis 215 of the cannula shaft 204. In a preferred embodiment, the groove or notch is configured to receive a cooperating protruding element (not shown) disposed on a guide sub-system 300 when the guide sub-system 300 is positioned in the cannula spacer 230 and sub-system 200, whereby rotational movement of the suture guide sub-system 300 with respect to the cannula spacer 230 and cannula sub-system 200a is constrained.

Suture Guide Sub-System

Figure 7A:
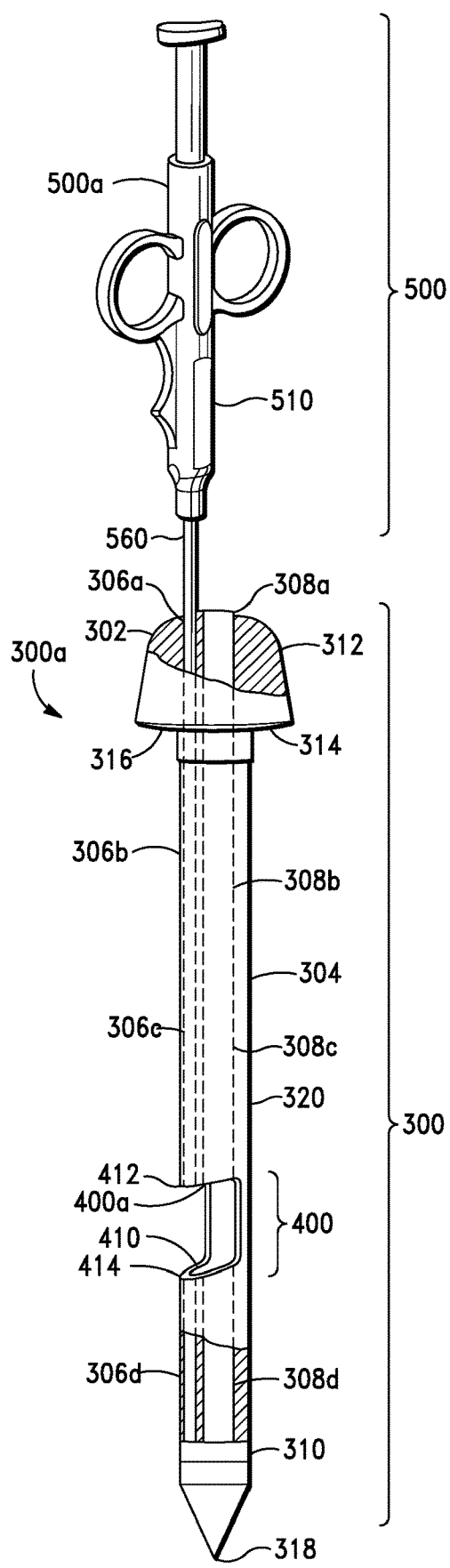
FIG. 7A is a front plan view of one embodiment of a suture guide sub-system with a cooperating suture passer sub-system, according to the invention.

Referring now to FIG. 7A, there is shown one embodiment of a suture guide sub-system 300a of the invention. As illustrated in FIG. 7A, the suture guide sub-system 300a comprises a guide base 302, comprising proximal and distal ends 312, 314 and a guide shaft 304, which comprises proximal and distal ends 316, 310, and one embodiment of a tissue positioning sub-system 400a of the invention.

As further illustrated in FIG. 7A, the guide base 302 includes a first suture lumen 306a and a first access lumen 308a, which extend from the proximal end 312 to the distal end 314 of the guide base 302, and the guide shaft 304 includes a second suture lumen 306b and a second access lumen 308b, which extend from the proximal end 316 of the guide shaft 304 to the proximal end 412 of the notch 410.

In a preferred embodiment of the invention, the first and second suture lumens 306a, 306b comprise the same diameter and are in an aligned relationship (forming a continuous suture lumen 306c) when the guide base 302 is engaged to the guide shaft 304, i.e., the guide shaft proximal end 316 is in direct communication with, i.e., secured to, the base distal end 314.

As discussed in detail below, the first and second suture lumens 306a, 306b and, hence, continuous suture lumen 306c are sized and configured to receive a suture passer sub-system 500 of the invention therein.

In some envisioned embodiments of the invention, continuous suture lumen 306c includes at least one continuous suture track or relief (not shown) that is contiguous with the continuous suture lumen 306c. According to the invention, the suture track facilitates smooth movement of a suture 102 engaged to a suture passer sub-system of the invention, e.g., suture passer sub-system 500, discussed below, through the continuous suture lumen 306c, when the suture passer sub-system is inserted in the continuous suture lumen 306c.

In a preferred embodiment of the invention, the it and second access lumens 308a, 308b also comprise the same diameter and are in an aligned relationship (forming a continuous access lumen 308c) when the guide base 302 is engaged to the guide shaft 304, i.e., the guide shaft proximal end 316 is in direct communication with, i.e., secured to, the base distal end 314.

As discussed in detail herein, the first and second access lumens 3084, 308b and, hence, continuous access lumen 308 are sized and configured to provide an access port for surgical instruments, e.g., endoscope, that facilitates entry thereof into a body cavity when a guide sub-system 300 of the invention is positioned therein.

As further illustrated in FIG. 7A, in some embodiments of the invention, the suture guide sub-system 300a also comprises a dilating tip 318 that is disposed on the distal end 310 of the guide shaft 304. According to the invention, the dilating tip 318 can comprise various configurations, including, but not limited to, conical, arrow-tipped and unibit shapes.

In some embodiments, the dilating tip 318 comprises a bladed tip. In a preferred embodiment, the dilating tip 318 comprises a bladeless tip to reduce trauma or damage to biological tissue when the guide sub-system 300a is deployed therein.

In some embodiments, the dilating tip 318 is removeably secured to the distal end 310 of the guide shaft 304. In some embodiments, dilating tip 318 is permanently secured to the distal end 310 of the guide shaft 304.

According to the invention, the dilating tip 318 can also comprise various conventional materials, including, but not limited to, any of the aforementioned metal and polymeric materials.

In some embodiments, the dilating tip 318 comprises a transparent or translucent material that allows an endoscope or other optical device to conduct imaging therethrough.

According to the invention, the guide shaft 304 can similarly comprise various diameters and lengths. In a preferred embodiment, the outer diameter of the guide shaft 304 is slightly less than the diameter of the continuous cannula lumen 208c, whereby the guide shaft 304 can be inserted therein. More preferably, the tolerance or clearance between the guide shaft 304 and continuous cannula lumen 208c when the guide shaft 304 is disposed therein is in the range of approximately 0.1-0.5 mm.

In some embodiments, the guide shaft 304 preferably comprises a length in the range of approximately 1-500 mm. In a preferred embodiment, the length of the guide shaft 304 is in the range of approximately 75-200 mm.

In some embodiments of the invention, the guide shaft 304 similarly comprises textured features on at least a portion of the guide shaft exterior surface 320 to reduce the risk of accidental dislodgment of the suture guide sub-system 300a from biological tissue or a tissue structure.

In some embodiments, at least a portion of the guide shaft exterior surface 320 comprises an outer coating that cases entry into and through body tissue or stabilizes the guide shaft 304 when positioned in body tissue and/or a body cavity, i.e., restricts translation of the guide shaft 304 when positioned in body tissue. Suitable coatings similarly comprise, without limitation, PTFE and parylene coatings.

Referring now to FIGS. 7B-7H, in some envisioned embodiments, the suture guide sub-system 300a, i.e., guide shaft 304, comprises adjustable tissue capture means 405, which, as discussed in detail below, is configured and positioned to facilitate and enhance tissue capture by the tissue positioning sub-system 400a.

In some embodiments, the distal end 314 of the suture guide sub-system 300a is configured to releasably engage the proximal end 212 of the cannula sub-system base member 20.

In some embodiments, the suture guide sub-system 300a further comprises an operator actuated lock and release mechanism that operates in conjunction with cannula sub-system 200a to removeably secure the suture guide sub-system 300a to the cannula sub-system 200a. According to the invention, the lock and release mechanism can comprise any conventional lock and release mechanism applicable to a TAC system 100 of the invention, including, without limitation, a disengageable push lock or plunger lock.

As indicated above, in a preferred embodiment of the invention, the suture guide sub-systems 300 of the invention further comprise a tissue positioning sub-system 400, which is a seminal feature of the suture guide sub-systems 400 and, hence, TAC systems 100 of the invention.

Referring now to FIGS. 8A-8C, one embodiment of the tissue positioning sub-system 400a of the invention will be described in detail.

As illustrated in FIGS. 8A-8C, in a preferred embodiment of the invention, the tissue positioning sub-system 400a comprises a tissue positioning notch 410 that comprises proximal and distal ends 412, 414. In some embodiments, the notch 410 preferably has a length from the proximal and distal ends 412, 414 thereof in the range of approximately 1-15 mm.

As discussed in detail below, during operation of a TAC system 100 that includes suture guide sub-system 300a, the tissue positioning notch 410 is configured to engage and retain at least a portion of biological tissue between the proximal and distal ends 412, 414 of the notch 410, when the suture guide sub-system 300a is at least partially withdrawn from a biological tissue structure, e.g., an abdominal cavity.

As indicated above, in some embodiments, the suture guide sub-system 300a further comprises adjustable tissue capture means 405 that is configured and positioned to facilitate and enhance engagement of biological tissue by the tissue positioning sub-system 400*a*, i.e., within tissue positioning notch 410.

Figure 7B:
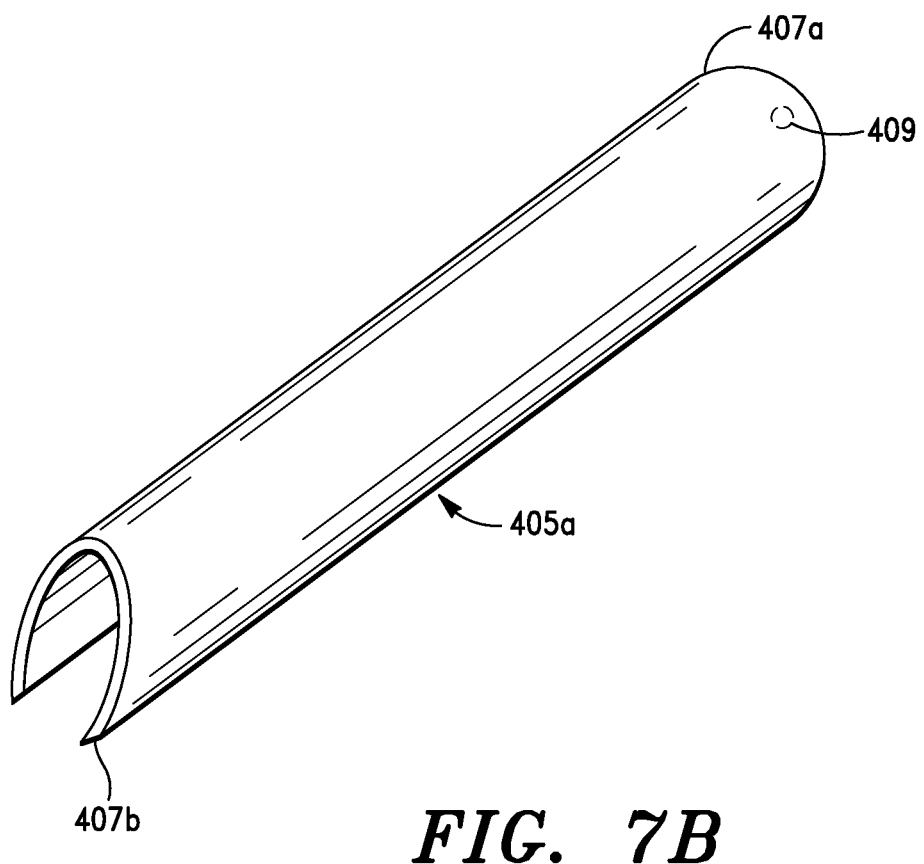
FIG. 7B is a perspective view of one embodiment of adjustable tissue capture means, according to the invention.
Figure 7C:
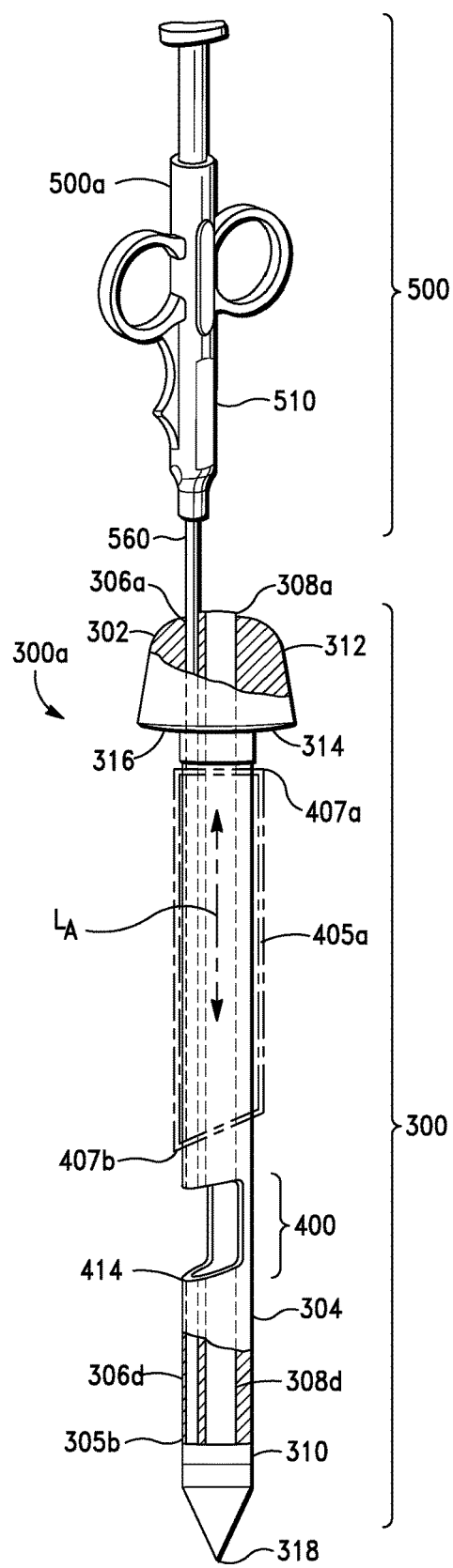
FIGS. 7C and 7D are front plan views of the suture guide sub-system shown in FIG. 7A, employing the adjustable tissue capture means shown in FIG. 7B, according to the invention.
Figure 7D:
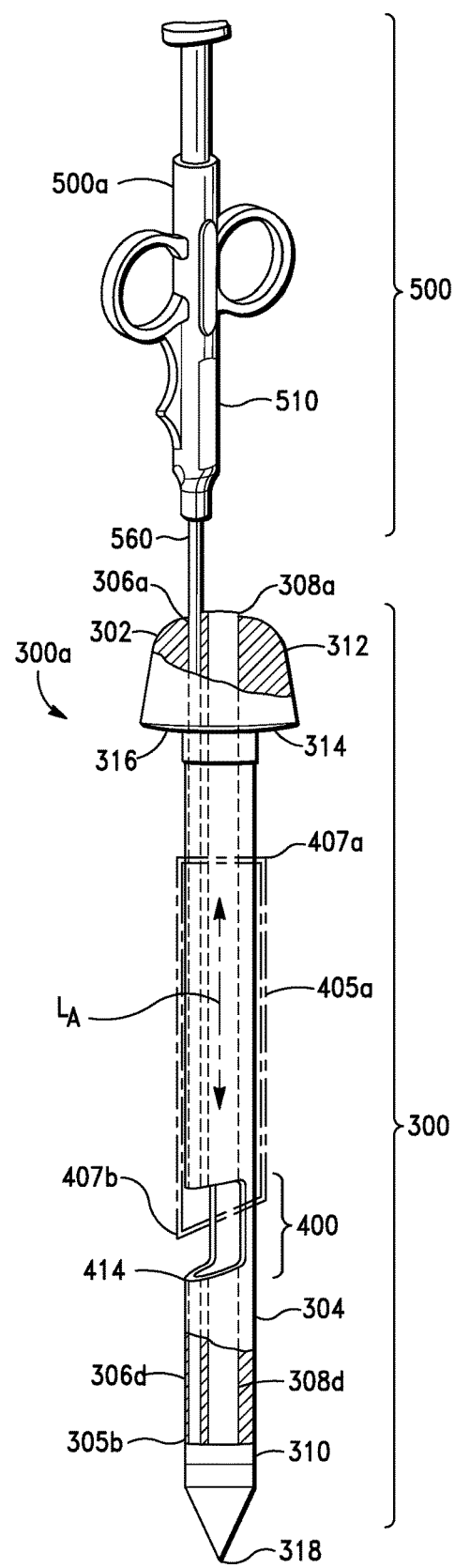

Referring now to FIGS. 7B-7D, there is shown one embodiment of an adjustable tissue capture means 405 of the invention. As illustrated in FIGS. 7B-7D, the adjustable tissue capture means 405 comprises an outer sleeve member 405*a* (shown in phantom in FIGS. 7C and 7D) that is sized and configured to be slidably positioned over guide shaft 304 and translate linearly along the central axis of the guide shaft 304, as shown by arrow LA, whereby the outer sleeve member 405*a* modulates the size of the opening of the tissue positioning notch 410, as shown in FIG. 7D.

As further illustrated in FIG. 7B, the outer sleeve member 405*a* comprises proximal and distal ends 407*a*, 407*b*. In a preferred embodiment, the distal end 407*b* of the outer sleeve member 405 comprises a shape that substantially corresponds to the shape of notch distal end 414.

In a preferred embodiment, the outer sleeve member 405*a* and the guide shaft 304 further comprise cooperating lock and release engagement means that is configured to position and maintain the outer sleeve member 405*a* in pre-determined pre-release and actuation, e.g., tissue engagement, positions on the suture guide sub-system 300*a*.

In some embodiments, the cooperating lock and release engagement means comprises a cooperating dimple and recess system, wherein at least one dimple member 409 is disposed on the outer sleeve member 405*a* luminal (or interior) surface, as shown in FIG. 7B, which is configured and positioned to engage at least one pre-formed recess disposed on the exterior surface 320 of the guide shaft 304.

In a preferred embodiment of the invention, the outer sleeve member 405 is adapted to be manually released from and positioned by the dimple and recess system.

Figure 7E:
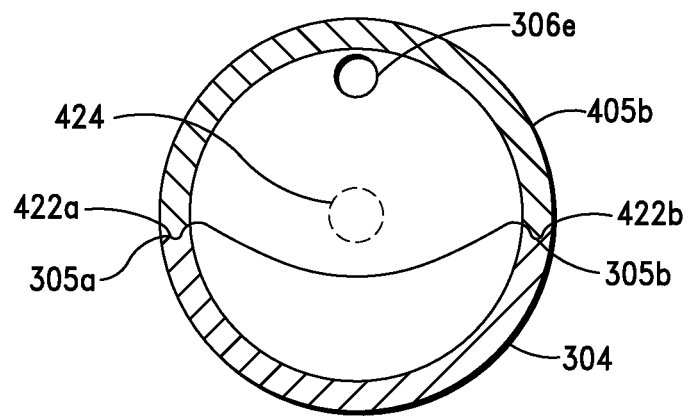
FIG. 7E is a front sectional view of another embodiment of adjustable tissue capture means, according to the invention.
Figure 7F:
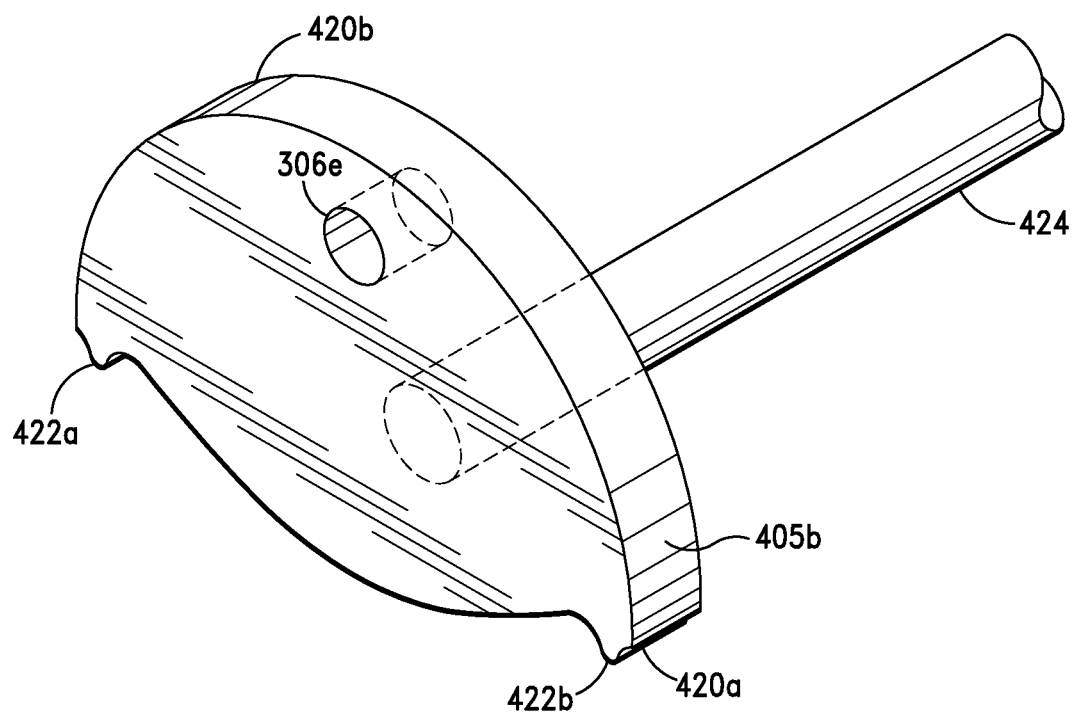
FIG. 7F is a partial perspective view of the adjustable tissue capture means shown in FIG. 7E, according to the invention.
Figure 7G:
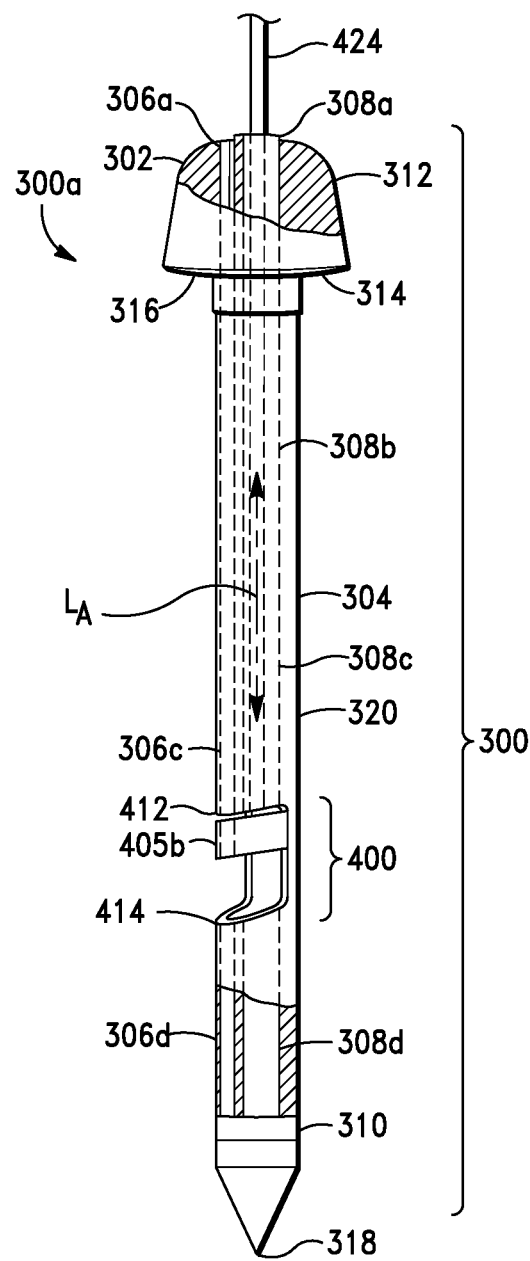
FIGS. 7O and 7H are front plan views of the suture guide sub-system shown in FIG. 7A, employing the adjustable tissue capture means shown in FIGS. 7E and 7F, according to the invention.
Figure 7H:
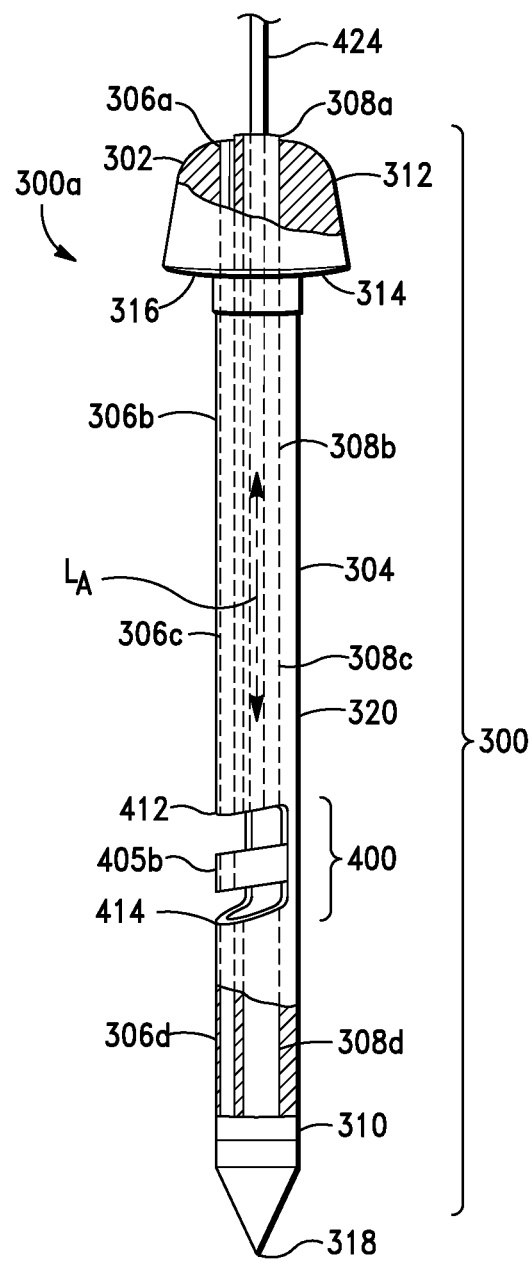

Referring now to FIGS. 7E-7H, there is shown another embodiment of an adjustable tissue capture means 405 of the invention. As illustrated in FIGS. 7E-7H, the adjustable tissue capture means 405 comprises a jaw member 405*b* that is sized and configured to be slidably positioned within notch 400*a* and translate linearly along the central axis of the guide shaft 304, as shown by arrow LA, whereby the proximal jaw member 405*b* similarly modulates the size of the opening of the tissue positioning notch 410, as shown in FIG. 7H.

Referring now to FIGS. 7E and 7F, in a preferred embodiment of the invention, the jaw member 405*b* comprises an outer shape that corresponds with the outer shape of the guide shaft 304.

As illustrated in FIGS. 7E and 7F, the jaw member 405*b* further comprises proximal and distal ends 420*a*, 420*b*, a lumen 306*c*, which is in alignment with continuous suture lumen 306*c*, and a drive shaft 424.

In a preferred embodiment, the jaw member 405*b* further comprises guide shaft guides 422*a*, 422*b*, which are sized and configured to seat and translate in cooperating guide shaft seats 305*a*, 305*b* to facilitate smooth translation of the jaw member 405*b* in the notch region.

As illustrated in FIGS. 7O and 7H, drive shaft 424 is connected to the proximal end 420*b* of the jaw member 405*b* and extends through the guide shaft 304. In one embodiment, such as illustrated in FIGS. 7O and 7H, the drive shaft 424 extends and translates through the continuous access lumen 308*c*.

As further illustrated in FIGS. 7G and 7K the drive shaft 424 extends out of the guide shaft 304 to facilitate actuation of the drive shaft 424 and, hence, jaw member 405*b*.

According to the invention, the drive shaft 424 and, hence, jaw member 405*b* can be modulated via various conventional actuation means, including, without limitation, manual actuation means.

In a preferred embodiment, the jaw member 405*b* and the guide shaft 304 similarly further comprise cooperating lock and release engagement means that is configured to position and maintain the jaw member 405*b* in pre-determined pre-release and actuation, e.g., tissue engagement, positions.

According to the invention, various conventional lock and release engagement means can be employed within the scope of the invention to position and maintain the jaw member 405*b* in pre-determined pre-release and actuation positions, including, without limitation, ratchet and one-way ball or roller bearing clutch systems.

As further illustrated in FIGS. 7A and 8A-8C, disposed proximate the proximal and distal ends 412, 414 of the notch 410 are continuous suture lumen 306*c* and suture lumen 306*d*, which is in an aligned relationship with continuous suture lumen 306*c*.

Referring now to FIGS. 8A-8C, in a preferred embodiment, the tissue positioning sub-system 400*a* comprises a capture clip 402 that is positioned at an internal location of the guide shaft 304 proximate the distal end 414 of the tissue positioning notch 410.

As illustrated in FIGS. 8A-8C, the capture clip 402 includes an extended region 404 that is disposed proximate the tissue positioning notch 410 such that the extended region 404 intersects the longitudinal axis of suture lumen 306*d*, where the extended region 404 forms a suture capture door (or system) 403. According to the invention, the capture door 403 is positioned and configured to capture a suture transferred into suture lumen 306*d* of the guide shaft 304 by a tissue passer sub-system 500 during operation of a TAC system 100 of the invention, i.e., when a suture passer sub-system 500 of the invention guides a suture 102 into and through continuous suture lumen 306*c*, notch 410 and suture lumen 306*d*, the extended region 404 of the capture clip 402 (i.e., suture capture door 403)transitions, i.e., is deflected or flexed, to an open position by the suture passer sub-system 500 as the distal end of the suture passer sub-system 500 (with a suture 102 engaged thereto) traverses beyond the distal end 414 of the tissue positioning notch 410. When the suture passer sub-system 5 is withdrawn from suture lumen 306*d*, the extended region 404 of the capture clip 402 (i.e., suture capture door 403) transitions back to a closed position and captures the suture 102.

In a preferred embodiment of the invention, the capture clip 402 further comprises an open region 408 which, when the capture clip 402 is positioned in the guide shaft 304, is in an aligned relationship with access lumen 308*d* (which is in an aligned relationship with continuous access lumen 308*c*) allows surgical instruments, such as an endoscope, to enter into and through access lumen 308*d* and guide shaft 304.

According to the invention, the capture clip 402 can further comprise structural features, such as formed ribs, which are designed to enhance the structural integrity of the thin section created by the notch 410.

In a preferred embodiment of the invention, the force (F) required to transition the extended region 404 of the capture clip 402 from a closed position to an open position is in the range of approximately 0.1-5.0 lbs$_f$.

According to the invention, the capture clip member 402 can comprise various materials, including, without limitation, metal and polymeric materials. Thus, in some embodiments, the capture clip member 402 comprises stainless steel. In some embodiments, the capture clip 402 comprises a shape memory alloy, such as a nickel titanium alloy (e.g., Nitinol™).

In some embodiments, the capture clip 402 comprises a polymeric material, such as one of the aforementioned polymeric materials.

In some embodiments, not shown, the capture door system 403 comprises a manually operated gating mechanism. In such embodiments, the suture guide sub-system 300a comprises a slide mechanism that is configured to transition the extended region 404 of the capture clip 402 from a closed position to an open position.

Figure 9:
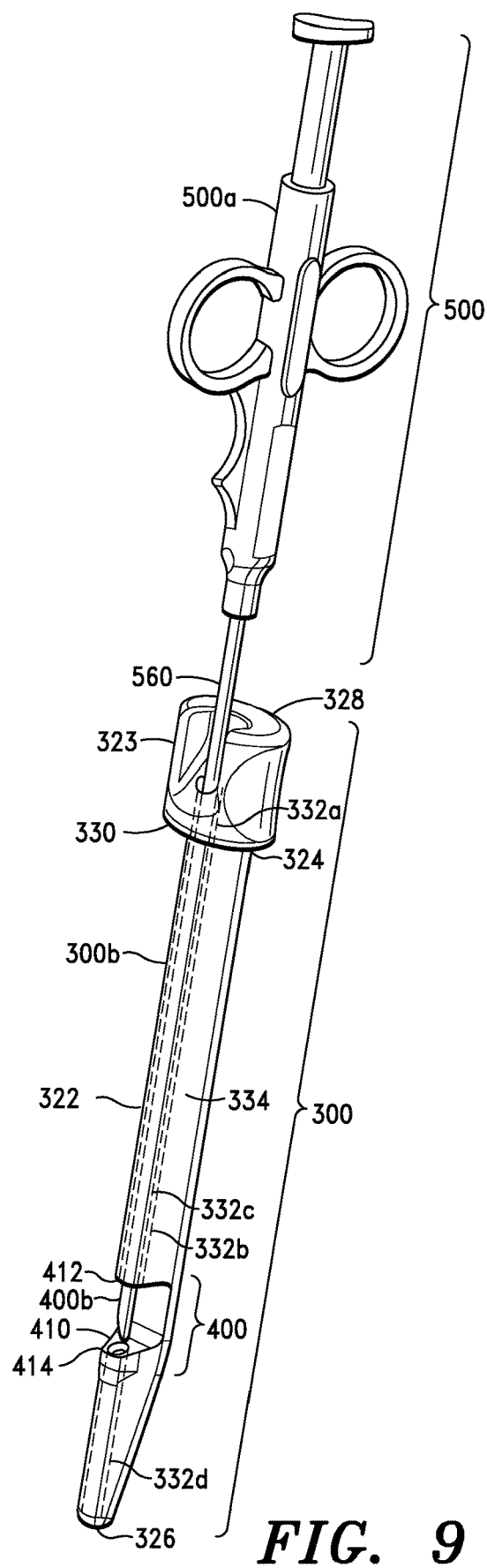
FIG. 9 is a perspective view of another embodiment of suture guide sub-system with a cooperating suture passer sub-system, according to the invention.
Figure 10:
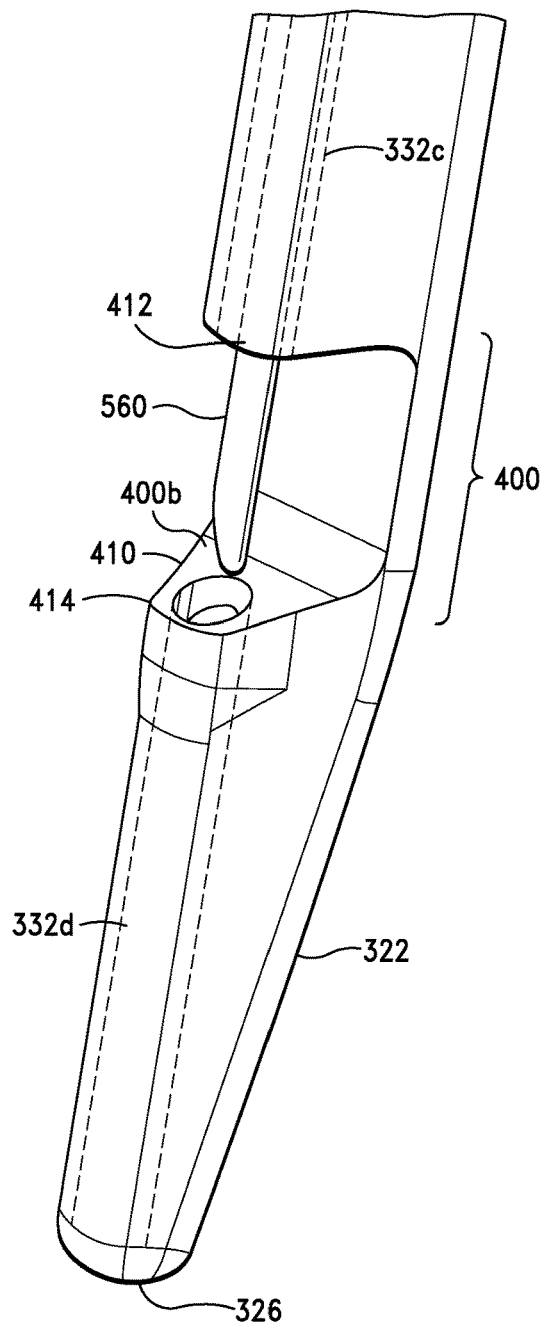
FIG. 10 is a partial perspective view of the suture guide sub-system shown in FIG. 9, illustrating another embodiment of a tissue positioning sub-system, according to the invention.

Referring now to FIGS. 9 and 10, there is shown another embodiment of a suture guide sub-system 300b of the invention. As illustrated in FIG. 9, the guide sub-system 300b similarly comprises a guide base 323, comprising proximal and distal ends 328, 330, and a guide shaft 322, which comprises proximal and distal ends 324, 326, and a tissue positioning sub-system 400b.

As further illustrated in FIGS. 9 and 10, the guide base 323 includes a first suture lumen 332a, which extends from the proximal end 328 to the distal end 330 of the guide base 323, and the guide shaft 322 includes a second suture lumen 332b, which extends from the proximal end 324 of the guide shaft 322 to the proximal end 412 of the notch 410.

In a preferred embodiment of the invention, the first and second suture lumens 332a, 332b similarly comprise approximately the same diameter and are in an aligned relationship (forming a continuous suture lumen 332c) when the guide base 323 is engaged to the guide shaft 322, i.e., the guide shaft proximal end 324 is in direct communication with, i.e., secured to, the base distal end 330.

As discussed in detail below, the first and second suture lumens 332a, 332b and, hence, continuous suture lumen 332c are also sized and configured to receive a suture passer sub-system 500 of the invention therein.

In a preferred embodiment of the invention, continuous suture lumen 332c includes at least one continuous suture track or relief that is contiguous with (and, hence, in a parallel relationship with) the continuous suture lumen 332c. According to the invention, the suture track similarly facilitates smooth movement of a suture 102 engaged to a suture passer sub-system 500 of the invention through the continuous suture lumen 332c, when the suture passer sub-system 500 is inserted in the continuous suture lumen 332c.

In some embodiments, the continuous suture lumen 332c comprises a single suture track or relief.

Figure 11:
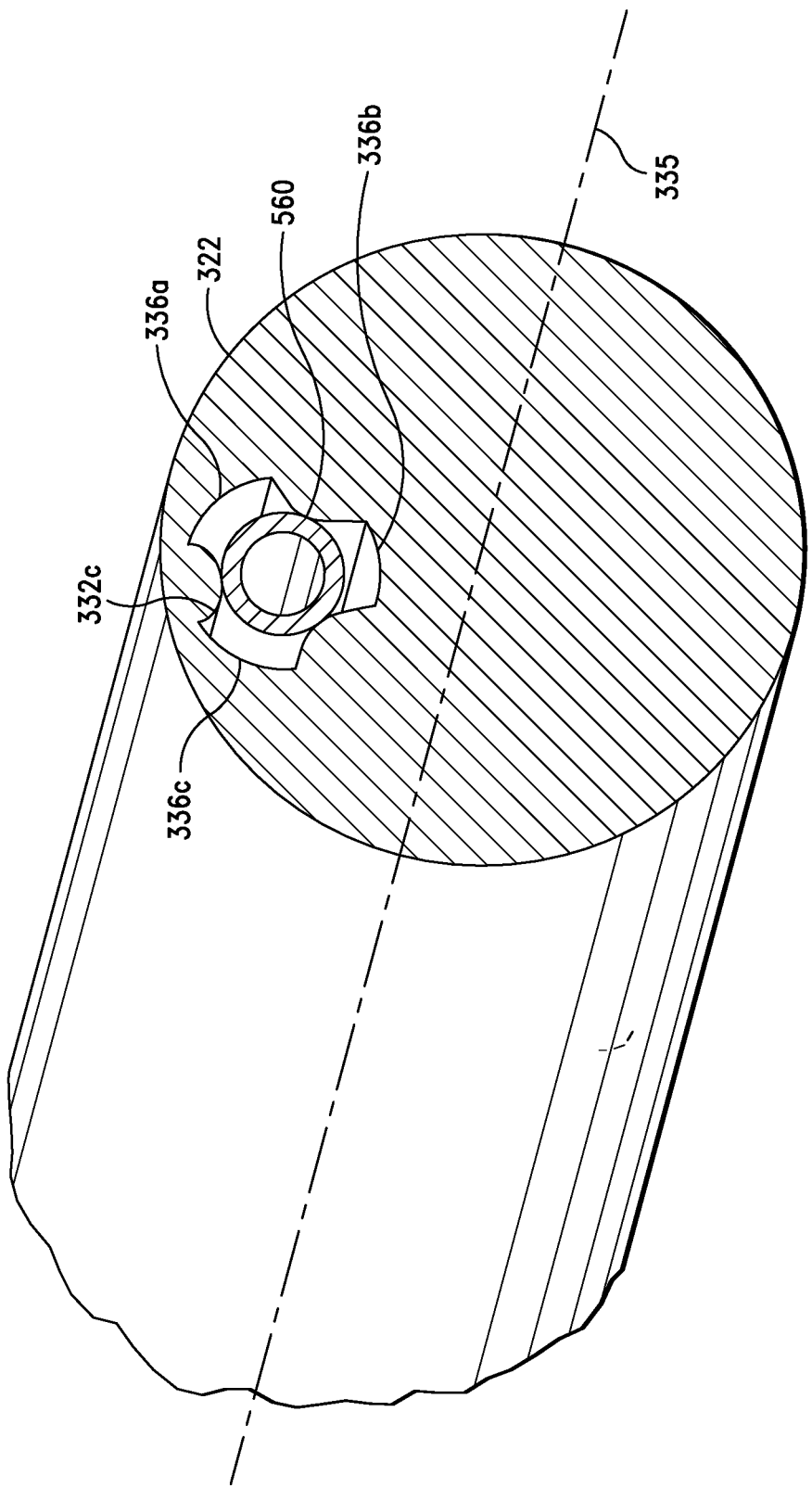
FIG. 11 is a partial perspective, sectional view of the suture guide sub-system shown in FIG. 9, illustrating one embodiment of a continuous internal lumen therein, according to the invention.

As illustrated in FIG. 11, in a preferred embodiment of the invention, continuous suture lumen 332c comprises three (3) suture tracks or reliefs 336a, 336b, 336c.

According to the invention, the distal end 326 of the guide shaft 322 can similarly comprise various configurations, including, but not limited to, conical, pyramid and unibit shapes.

In some embodiments, the distal end 326 comprises a bladed tip. In a preferred embodiment, the distal end 326 comprises a bladeless tip to reduce trauma or damage to biological tissue when the suture guide sub-system 300b is deployed therein.

According to the invention, the guide shaft 322 can similarly comprise various diameters and lengths. In some embodiments, the diameter of the guide shaft 322 is similarly slightly less than the diameter of the continuous cannula lumen 20, whereby the guide shaft 322 can be inserted therein. More preferably, the tolerance or clearance between the guide shaft 322 and continuous cannula lumen 208c when the guide shaft 322 in disposed therein is similarly in the range of approximately 0.1-1.0 mm.

According to the invention, the suture guide sub-system 300b can also comprise a stand-alone suture guide system, i.e., the guide sub-system 300b can be employed to directly access and close tissue without the use of a cannula sub-system 200.

In some embodiments, the guide shaft 322 similarly preferably comprises a length in the range of approximately 1-500 mm. In a preferred embodiment, the length of the guide shaft 322 is in the range of approximately 100-200 mm.

In some embodiments of the invention, the guide shaft 322 similarly comprises textured features on at least a portion of the guide shaft exterior surface 334 to reduce the risk of accidental dislodgment of the suture guide sub-system 300b from biological tissue or tissue structure.

In some embodiments, at least a portion of the guide shaft exterior surface 334 comprises an outer coating that eases entry into and through body tissue or stabilizes the guide shaft 322 when positioned in body tissue and/or a body cavity, i.e., restricts translation of the guide shaft 322 when positioned in body tissue. Suitable coatings similarly comprise, without limitation, PTFE and parylene coatings.

In some embodiments, the suture guide sub-system 300b further comprises an operator actuated lock and release mechanism that operates in conjunction with cannula sub-system 200 to removeably secure the suture guide sub-system 300b to the cannula sub-system 200. According to the invention, the lock and release mechanism can similarly comprise any conventional lock and release mechanism applicable to a TAC system 100 of the invention, including, without limitation, a disengageable push lock or plunger lock.

As indicated above, in a preferred embodiment of the invention, the suture guide sub-system 300b also comprises a tissue positioning sub-system 400b.

Figure 13:
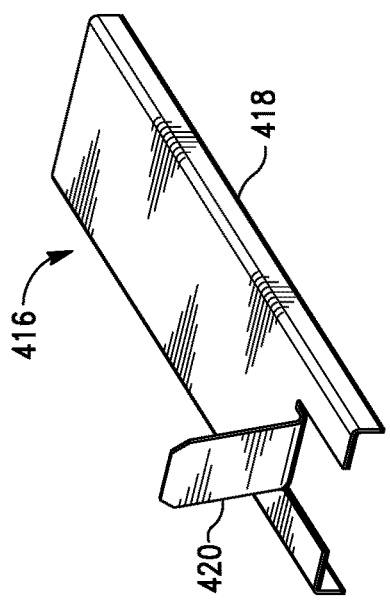
FIG. 13 is a perspective view of one embodiment of a suture capture clip that is configured to cooperate with the suture capture door system shown in FIGS. 12A and 12B, according to the invention.
Figure 12B:
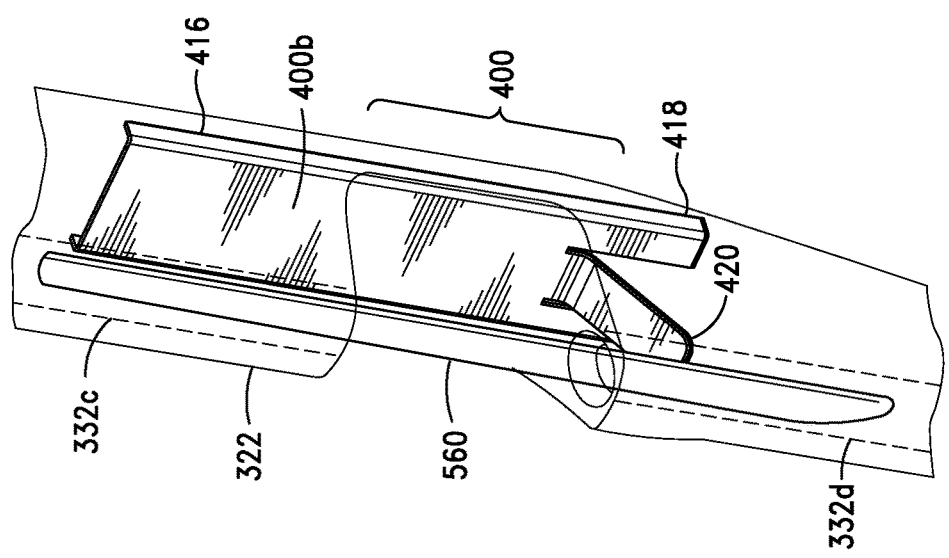
FIGS. 12A and 12B are partial perspective views of the suture guide sub-system shown in FIG. 9, illustrating the suture capture clip of the suture capture door system of the suture guide sub-system that is shown in FIG. 10, according to the invention.
Figure 12A:
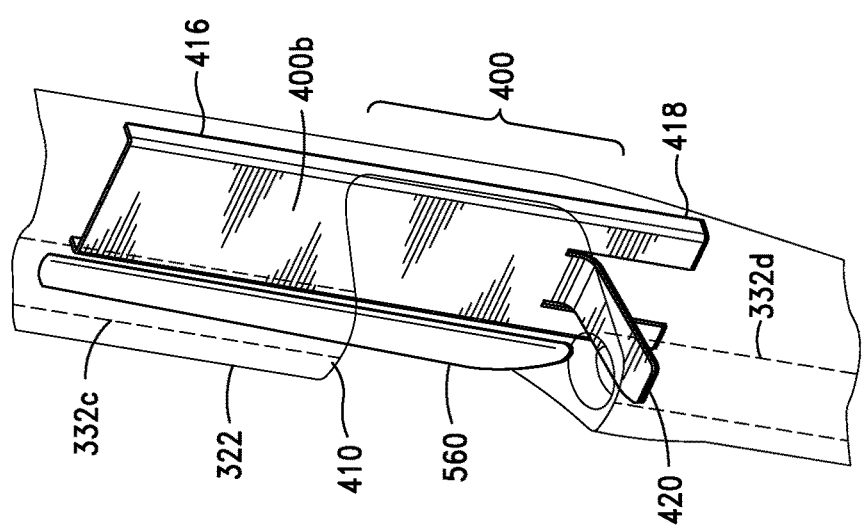

Referring now to FIGS. 12A, 12B and 13, the tissue positioning subsystem 400b will be described in detail.

As illustrated in FIGS. 12A, 12B and 13, in a preferred embodiment of the invention, the tissue positioning sub-system 400b similarly comprises tissue positioning notch 410, which, as indicated above, is configured to engage and retain at least a portion of biological tissue between the proximal and distal ends 412, 414 of the notch 410 when the guide sub-system 300b is at least partially withdrawn from a biological tissue structure, e.g., an abdominal cavity.

As further illustrated in FIGS. 9,10,12A and 12B, disposed proximate the proximal and distal ends 412, 414 of the notch 410 are continuous suture lumen 332e and suture lumen 332d, which is in an aligned relationship with continuous suture lumen 332e.

As illustrated in FIG. 11, in a preferred embodiment, suture lumen 332d also comprises continuous grooves or notches 336a, 336b, 336c. In some embodiments, suture lumen 332d comprises a plurality of continuous grooves or notches. In some embodiments, the suture lumen 332d comprises a single continuous groove or notch.

Referring now to FIGS. 12A, 12B and 13, in a preferred embodiment, the tissue positioning subsystem 400b also comprises a capture clip 416 that is positioned at an internal location of the guide shaft 322 proximate the distal end 414 of the tissue positioning notch 410.

As illustrated in FIGS. 12A, 12B and 13, the capture clip 416 similarly includes an extended region 420 that is disposed proximate the suture lumen 332d, where the extended region 420 similarly forms a suture capture door (or system) 418.

In a preferred embodiment, the suture capture door 418 similarly facilitates the capture of a suture transferred into suture lumen 332d of the guide shaft 322 by a tissue passer sub-system 500 in a manner that is similar to suture capture door 403 discussed above, i.e., when a suture passer sub-system 500 of the invention guides a suture 102 into and through continuous suture lumen 332e, notch 410 and suture lumen 332d, the extended region 420 of the capture clip 416 transitions, i.e., is deflected or flexed, to an open position by the suture passer sub-system 500 as the distal end of the suture passer sub-system 500 (with a suture 102 engaged thereto) traverses beyond the distal end 414 of the tissue positioning notch 410. When the suture passer sub-system 500 is withdrawn from suture lumen 332d, the extended region 420 of the capture clip 416 (i.e., suture capture door 418)transitions back to a closed position and captures the suture 102.

According to the invention, the capture clip 416 can similarly comprise structural features, such as formed ribs, that are designed to enhance the structural integrity of the notch 410 region.

In a preferred embodiment of the invention, the force (F) required to transition the extended region 420 of the capture clip 416 from a closed position to an open position is similarly in the range of approximately 0.1-5.0 lbs$_f$.

According to the invention, the capture clip member 416 can also comprise various materials, including, without limitation, metal and polymeric materials. Thus, in some embodiments, the capture clip 416 comprises stainless steel. In some embodiments, the capture clip 416 comprises a shape memory alloy, such as a nickel titanium alloy (e.g., Nitinol™).

In some embodiments, the capture clip 416 comprises a polymeric material, such as one of the aforementioned polymeric materials.

According to the invention, the suture capture door system 418 can similarly comprise a manually operated gating mechanism. In such embodiments, the suture guide sub-system 300b includes a slide mechanism that is configured to transition the extended region 420 of the capture clip 416 from a closed position to an open position.

Suture Passer Sub-System

Referring now to FIGS. 14-16, 17A-17C, 18 and 19A-19D, there is shown one embodiment of a suture passer sub-system 500a of the invention. As illustrated in FIGS. 7 and 9, and discussed in detail herein, in a preferred embodiment, the suture passer sub-system 500a is adapted to cooperate with a suture guide sub-system 300 of the invention, such as suture guide sub-systems 300a and 300b.

Figure 14:
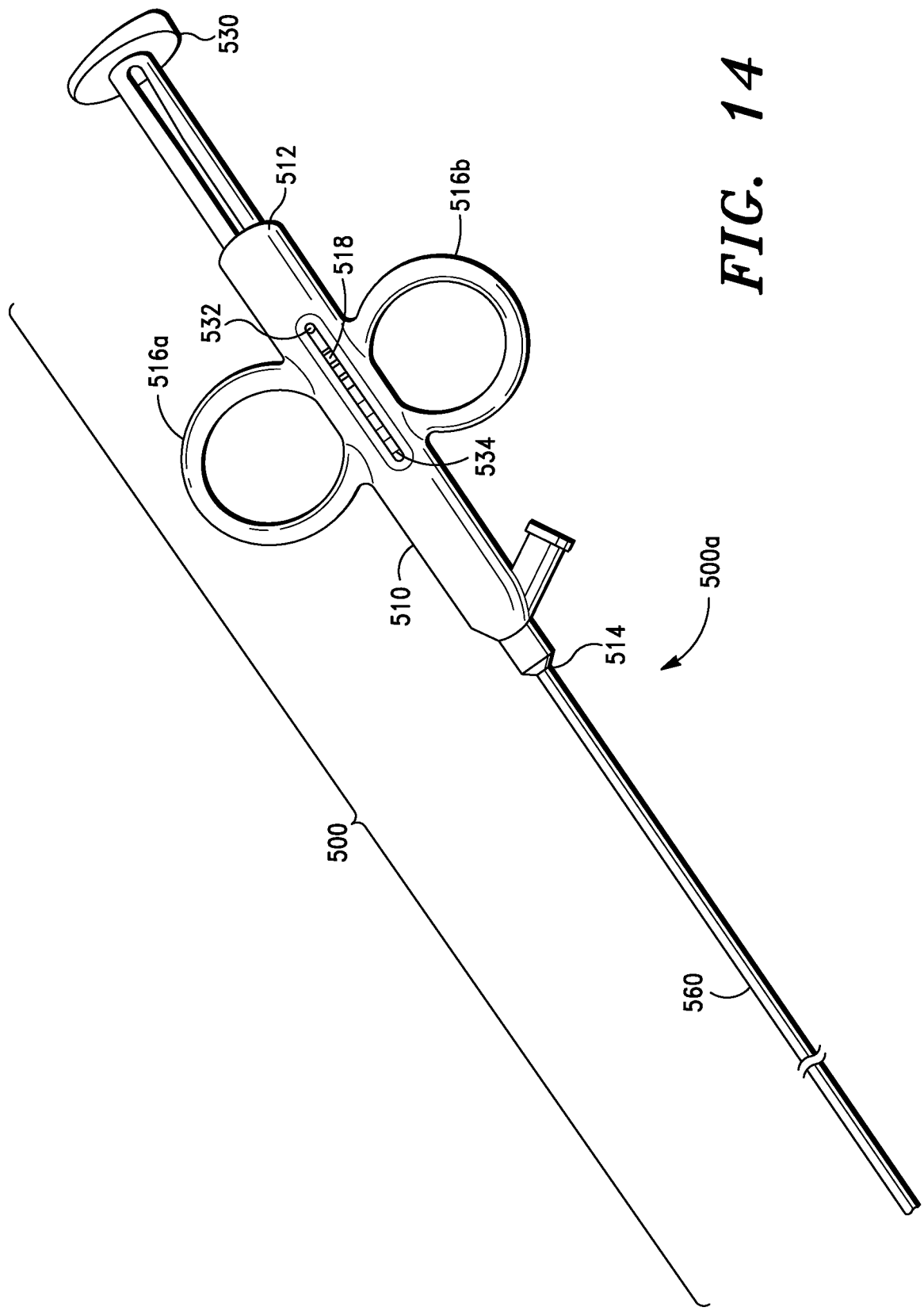
FIG. 14 is a perspective view of one embodiment of a suture passer sub-system, according to the invention.
Figure 15:
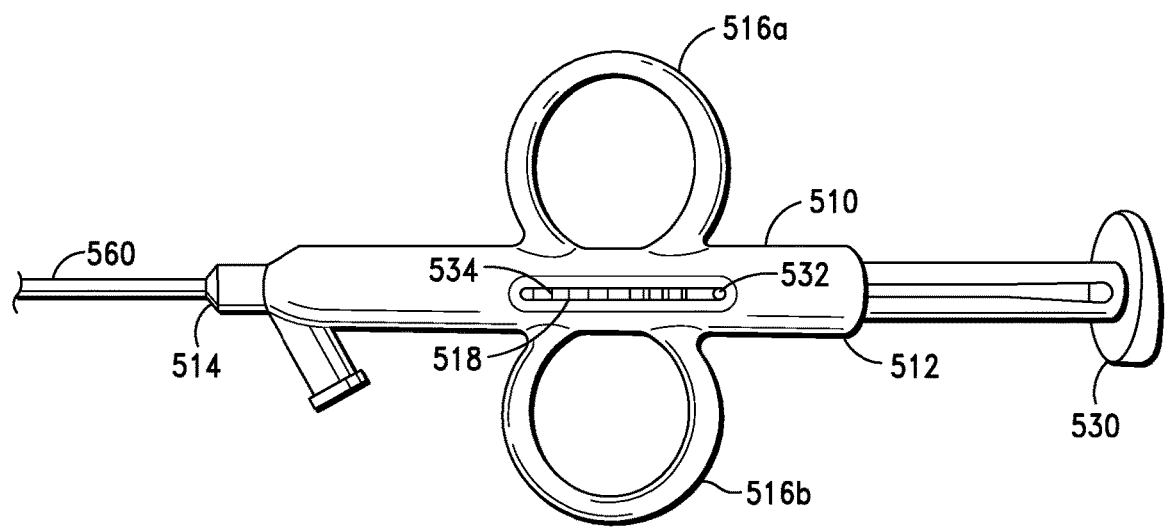
FIG. 15 is a partial front plan view of the suture passer sub-system shown in FIG. 14, illustrating the housing thereof, according to the invention.
Figure 16:
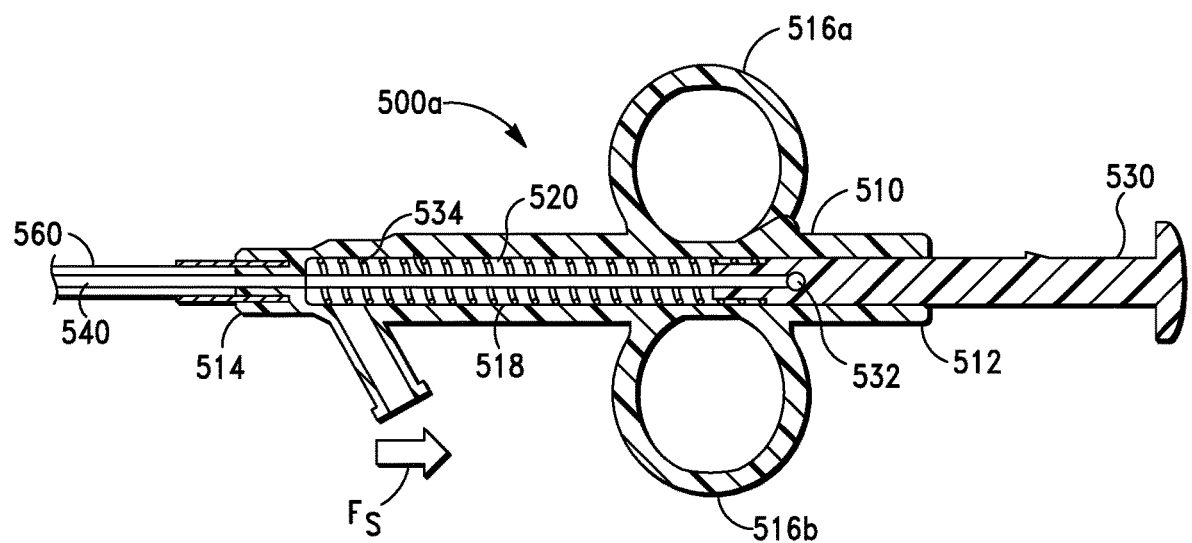
FIG. 16 is a partial front plan sectional view of the suture passer sub-system shown in FIG. 14, according to the invention.

As illustrated in FIGS. 14-16, in a preferred embodiment, the suture passer sub-system 500a comprises a housing (or handle) 510, actuator 530, compression spring 534, suture deployment shaft (i.e., needle) 540 and tubular cannula shaft 560, which is configured to receive the suture deployment shaft 540 therein.

As discussed in detail below and illustrated in FIG. 18, the suture deployment shaft 540 includes suture deployment and capture means 550 that is disposed on the distal end of the suture deployment shaft 540. In a preferred embodiment, the suture deployment and capture means 550 is configured to capture and removably secure a suture 102 therewith.

In some embodiments, the housing 510 comprises proximal and distal ends, 512, 514 at least one, more preferably, two (2) finger contours 516a, 516b to facilitate a controlled grip and manipulation of the suture passer sub-system 500a.

As illustrated in FIGS. 14 and 15, the actuator 530 and suture deployment shaft 540 are preferably joined (or coupled) via an actuator-deployment shaft pin 532, whereby, when a sufficient actuation force is exerted on the actuator 530, the suture deployment shaft 540 transitions from a retracted position (or state) to an extended position.

As also illustrated in FIGS. 14 and 15, the housing 510 further comprises a guide slot 518, which is preferably disposed adjacent finger contours 516a, 516b. According to the invention, the guide slot 518 is positioned and configured to receive the actuator-deployment shaft pin 532 and control travel of the actuator 530 and, hence, suture deployment shaft 540.

Referring now to FIG. 16, the interior of the housing 510 (denoted generally "520") is configured to receive, contain and provide structural support for the actuator 530, suture deployment shaft 540 and the compression spring 534. The distal end 514 of the housing 510 is further configured to receive and secure the cannula shaft 560 to the housing 510.

According to the invention, the compression spring 534 is positioned and configured to exert a spring force (denoted by arrow $F_s$) on the actuator 530 and, thereby, suture capture shaft 540, when the actuator 530 is in a static (i.e., retracted) state.

Preferably, the actuator 530 is able to axially advance the suture deployment shaft 540 inside of the cannula shaft 560 from a retracted position to an extended position with minimal force exerted on the actuator 530 with an operator's thumb. Thus, in a preferred embodiment, the spring force $(F_s)$ exerted on the actuator 530 by the compression spring 534 when the actuator 530 is in a static state is in the range of approximately 0.5-4.0 lbs$_f$.

As indicated above, in a preferred embodiment, the housing guide slot 518 is configured and sized to limit axial advancement of the actuator-deployment shaft pin 532 and, hence, suture deployment shaft 540, when an actuation force is exerted on the actuator 530 by an operator. Thus, full thumb force can be exerted on the actuator 530 by an operator without concern that the suture deployment shaft 540 will overextend.

Figure 17A:
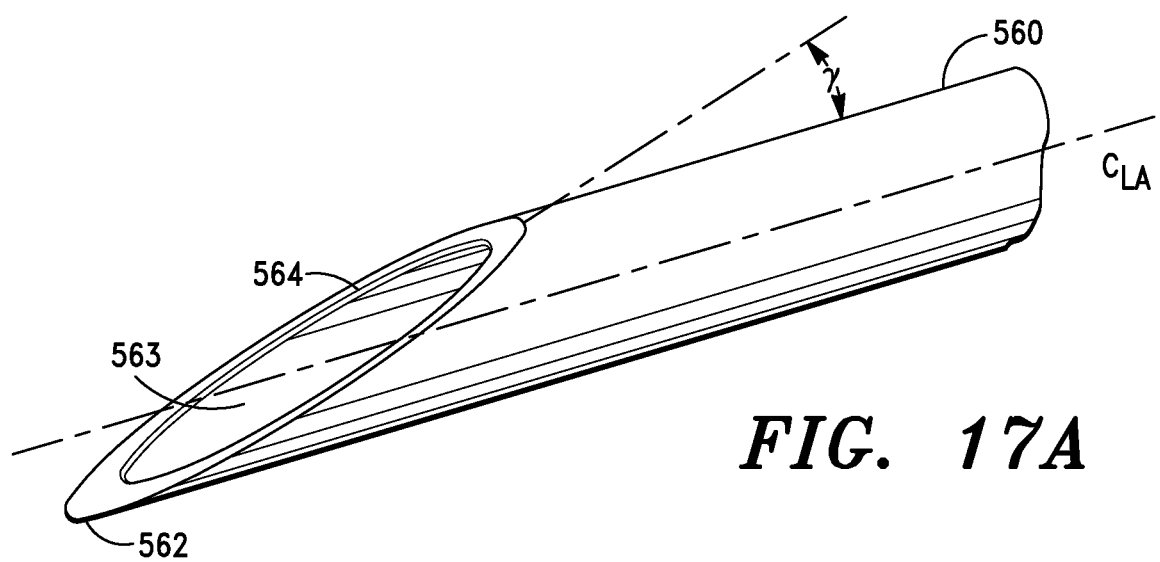
FIG. 17A is a partial perspective view of one embodiment of a suture passer sub-system cannula shaft, according to the invention.

Referring now to FIG. 17A, in a preferred embodiment of the invention, the cannula shaft 560 preferably includes a beveled edge 564 on the distal end 562 thereof which is configured to pierce through tissue to facilitate suture passage. In a preferred embodiment of the invention, the angle "γ" of the beveled edge 564 with respect to the longitudinal axis of the cannula shaft 560 (denoted "$C_{LA}$") is in the range of 10-40°.

According to the invention, the edge 564 of cannula shaft 560 can comprise various alternative shapes to facilitate piercing though tissue.

Figure 17B:
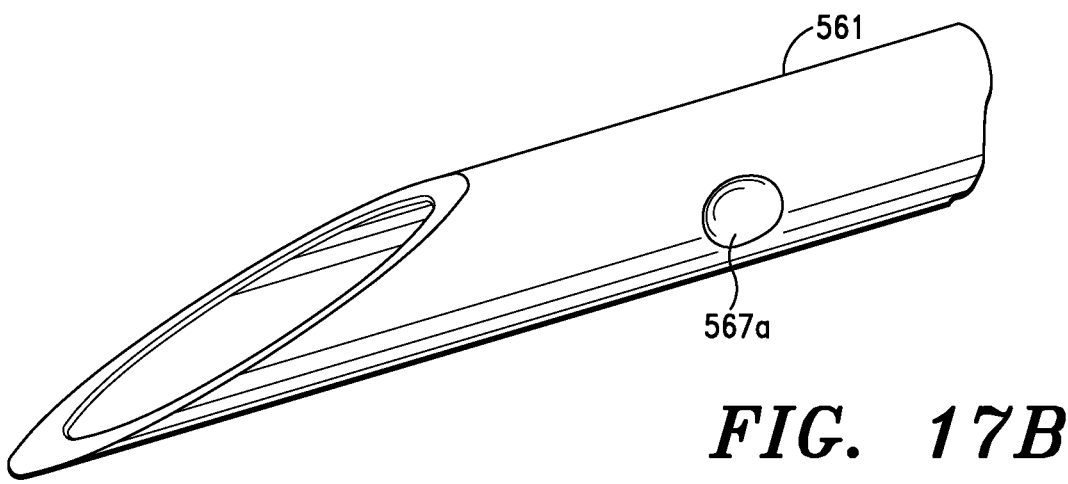
FIGS. 17B and 17C are partial perspective views of another embodiment of a suture passer sub-system cannula shaft, according to the invention.
Figure 17C:
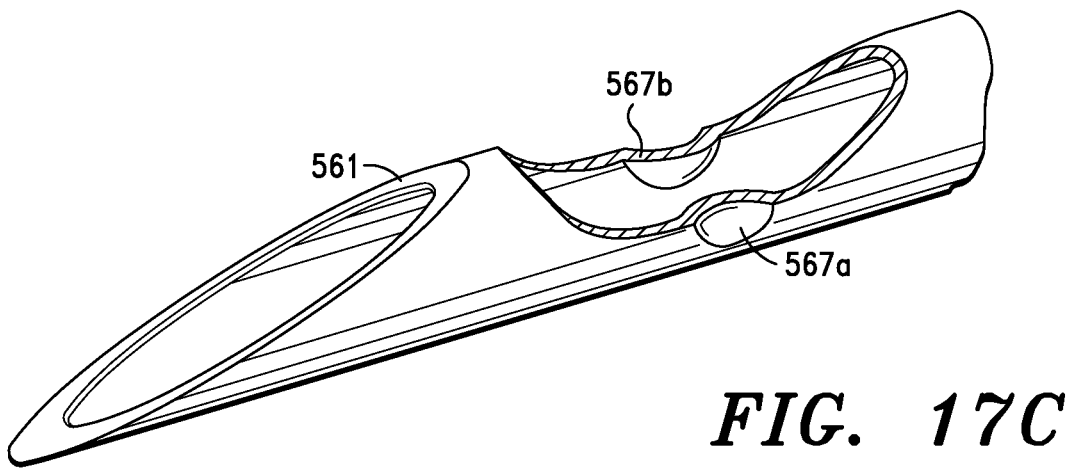

Referring now to FIGS. 17B and 17C, in some embodiments of the invention, the cannula shaft (now denoted "561") further comprises a pair of dimples 567a, 567b that are preferably disposed on opposing sides of the cannula shaft 561. According to the invention, the dimples 567a, 567b are sized and positioned on the cannula shaft 561 to facilitate the release of a captured suture 102 by the suture deployment and capture means 550 of the suture passer sub-system 500S, as discussed below.

As indicated above, the suture deployment shaft 540 includes suture deployment and capture means 550 that is configured to capture and removably secure a suture 102 therewith. As illustrated in FIG. 1, in a preferred embodiment, the suture deployment and capture means 550 comprises a tong member 551 having an elongated top portion 552 and a cooperating elongated bottom portion 554.

Figure 18:
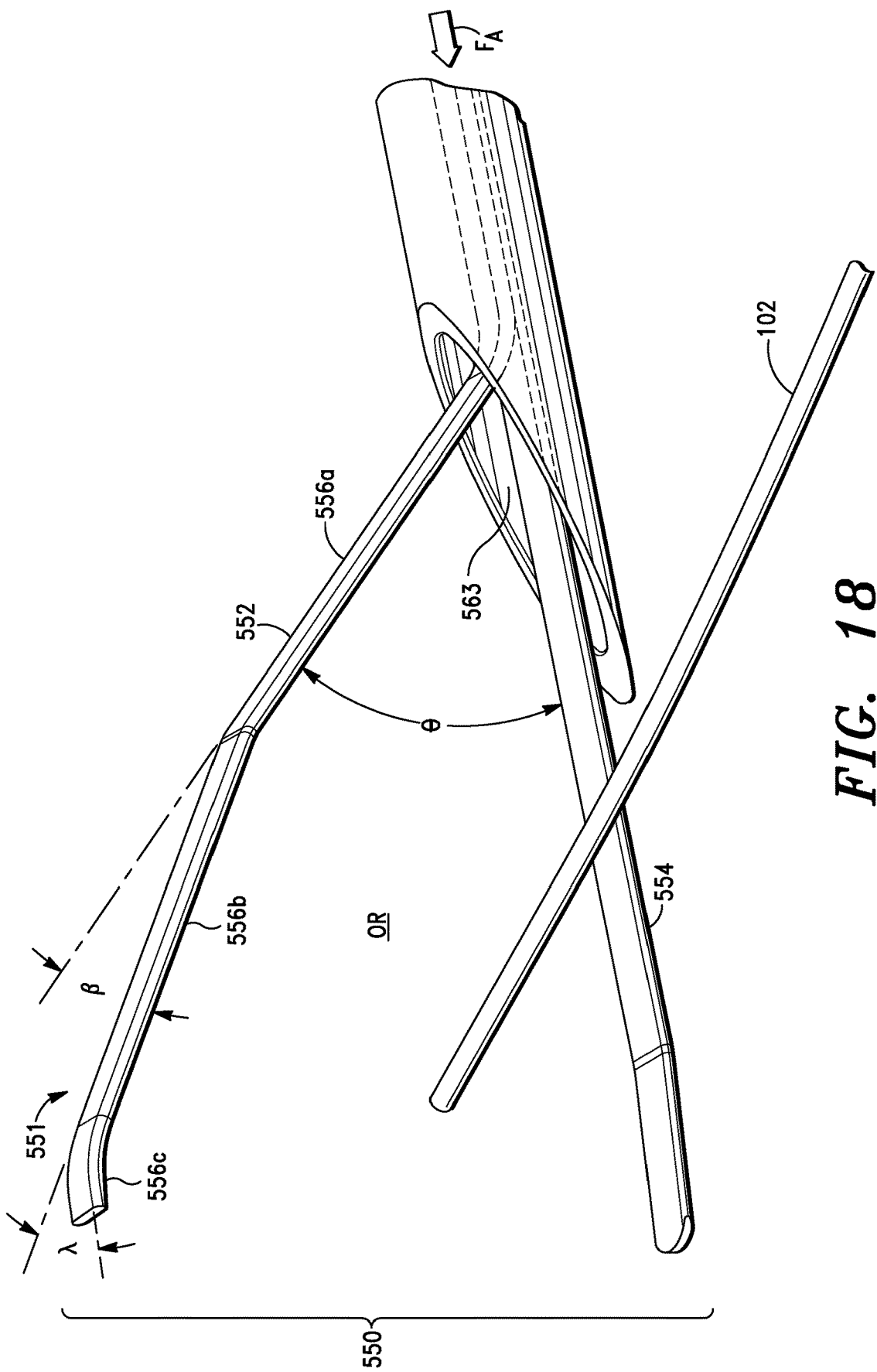
FIG. 18 is a partial perspective view of the cannula shaft shown in FIG. 17A, illustrating one embodiment of suture capture means, i.e., a tong member, extended out of the cannula shaft in an extended state, according to the invention.
Figure 19A:
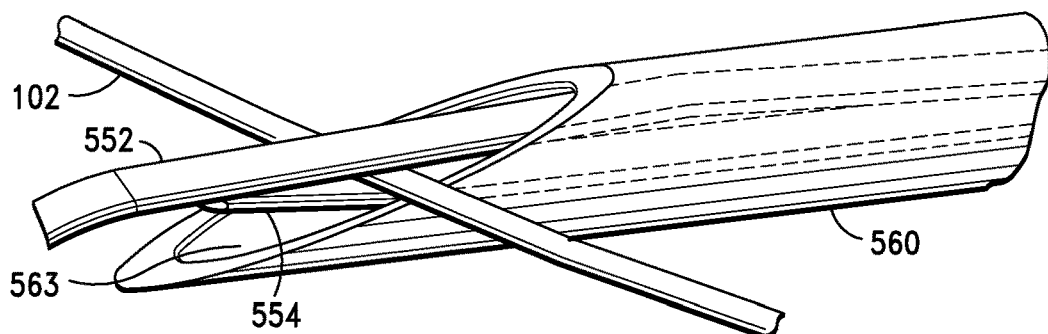
FIGS. 19A-19C are perspective views of the cannula shaft shown in FIGS. 17A and 18, illustrating a suture connected to the suture capture means and the suture capture means in several stages of retraction in the cannula shaft, according to the invention.
Figure 19B:
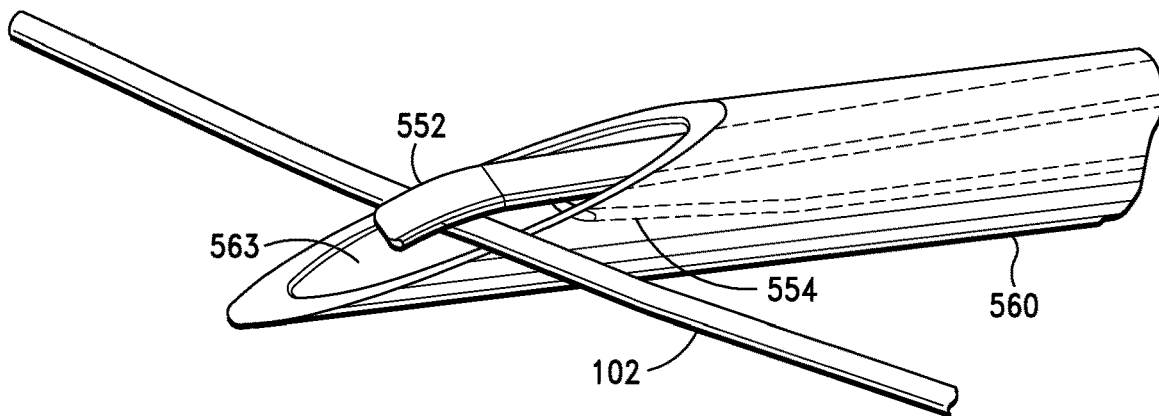
Figure 19C:
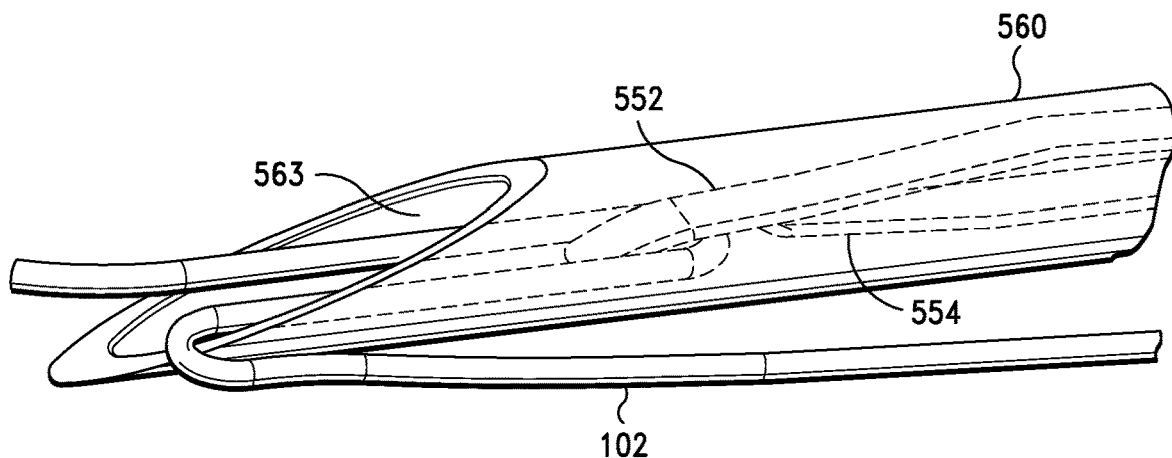

In a preferred embodiment of the invention, the elongated top and bottom portions 552, 554 of the tong member 551 are configured or pre-shaped to transition from a restrained static or pre-deployment configuration when the suture deployment shaft 540 is in a retracted position, wherein, as illustrated in FIG. 19C, the tong member 551 is disposed in the cannula lumen 563, to an expanded (or unrestrained) configuration, when the suture deployment shaft 540 is in an extended position and the tong member 551 is extending out of the cannula lumen 563, as illustrated in FIG. 18.

As further illustrated in FIG. 18, when the tong member 551 is in the extended position, the elongated top portion 552 is disposed at an angle θ with respect to the elongated bottom portion 554, whereby an open region (denoted "OR") is provided between the elongated top and bottom portions 552, 554 of the tong member 551.

As also illustrated in FIG. 18, in a preferred embodiment, the elongated top portion 552 of the tong member 551 comprises a first substantially linear segment 556a, a second substantially linear segment 556b, which is disposed at an angle β with respect to first segment 556a, and a linear distal end 556c, which is disposed at an angle λ with respect to the linear segment 556b.

In a preferred embodiment, angle β is in the range of 5°-15° to, as discussed below, provide a supplemental suture engagement force upon an engaged suture 102 when the tong member 551 is being retracted into the cannula lumen 563.

In a preferred embodiment, angle λ is in the range of 2°-30° to, as also discussed below, facilitate release of a suture 102 when the tong member 551 is in a restrained state, i.e., a static or pre-deployment configuration, in the cannula lumen 563.

Referring now to FIGS. 19A-19D, engagement of a suture 102 with the tong member 551 and release of the suture 102 therefrom will now be described in detail.

According to the invention, to facilitate initial suture capture, the suture deployment shaft 540 is axially advanced from a static/retracted position in the cannula lumen 563 to an extended position shown in FIG. 18 by exerting an actuation force on the actuator 530 in the direction denoted by arrow $F_A$, wherein the tong member 551 is exposed. As illustrated in FIG. 18, a suture 102 can then be positioned in the open region "OR" (i.e., seated in the open region) of the tong member 551.

After the suture 102 is seated in the open region "OR" of the tong member 551, the actuator 530 is released and the spring force $F_s$ exerted by the spring 534 on the actuator 530 withdraws (or retracts) the suture deployment shaft 540 and, hence, tong member 551 with the suture 102 connected thereto into the cannula shaft 560, as shown in FIGS. 19A and 19B.

As illustrated in FIG. 19A, during an initial retraction stage of the tong member 551, the elongated top and bottom portions 552, 554 of the tong member 551 collapse and capture the suture 102, and, preferably, pull the suture 102 against the beveled distal end 562 of the cannula 560.

As illustrated in FIG. 19B, further retraction of the tong member 551 enables the elongated bottom portion 554 of the tong member 551 to release the suture 102, while the elongated top portion 552, due to its greater bending moment, exerts a greater force on the suture 102 to pull the suture 102 against the beveled distal end 562 of the cannula 560.

As illustrated in FIG. 19C, further retraction of the tong member 551 enables the elongated top portion 552 of the tong member 551 to collapse and secure the suture 102 in and against the cannula shaft lumen 563. In a preferred embodiment of the invention, the lateral gap between the elongated portion 552 of the tong member 551 and the inside diameter of the cannula 560 ranges from 0.1 mm to 1.0 mm per side. A sufficient lateral gap enables the collapse of the suture 102, thus preventing premature release of the suture 102.

Figure 19D:
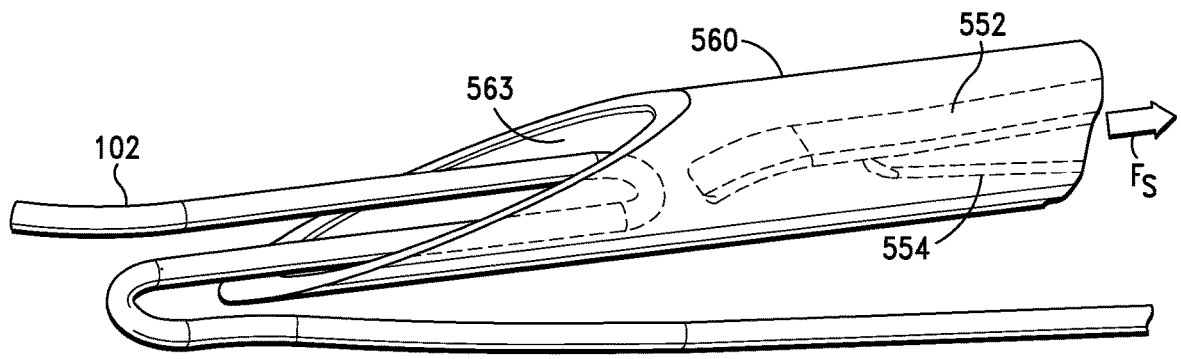
FIG. 19D is a further perspective view of the cannula shaft shown in FIGS. 17A and 18, illustrating the release of the suture from the suture capture means when the suture capture means is in a fully retracted state in the cannula shaft, according to the invention.

According to the invention, the retention force exerted on a suture 102 by the elongated top portion 552 of the tong member 551 when the tong member 551 is withdrawn into the cannula shaft 560 and, hence, is in a static/retracted position, wherein, as shown in FIG. 19C, the suture 102 is disposed between the elongated top portion 552 and the surface of the cannula shaft lumen 563, is preferably in the range of 0.01-5.0 $lbs_f$ to, as shown in FIG. 19D and discussed in detail below, allow the suture 102 to be readily released from the tong member 551 when captured by a suture capture door (i.e., 403 or 418) of a suture guide sub-system 300 of the invention.

In some embodiments of the invention, the maximum retention force exerted against a suture 102 by the elongated top portion 552 of the tong member 551 when the tong member 551 is withdrawn into the cannula shaft 560 is less than the closure force (F) of the suture capture door (403 and 418) of the suture guide sub-system 300.

According to the invention, by virtue of the design of the suture capture doors 403, 418, suture 102 can also be released from the tong member 551 and captured by a suture capture door 403 or 418 when the retention force exerted on a suture 102 by the elongated top portion 552 of the tong member 551 when the tong member 551 is withdrawn into the cannula shaft 560 is greater than the closure force (F) of the suture capture door (403 and 418) of the suture guide sub-system 300.

In a preferred embodiment of the invention, the beveled edge 564 of the cannula shaft 560 acts as a strain relief when force is pulled on the suture 102 in a proximal direction, such as when the suture capture shaft 540 with suture 102 engaged thereto is advanced through tissue. However, due to the shallow angle λ at the distal end of the elongated top portion 552 of the tong member 551, the force required to release the suture 102 is low, whereby the suture 102 can be readily released and captured by a suture capture door system (i.e., 403 or 418) of a suture guide sub-system 300 of the invention.

Figure 20A:
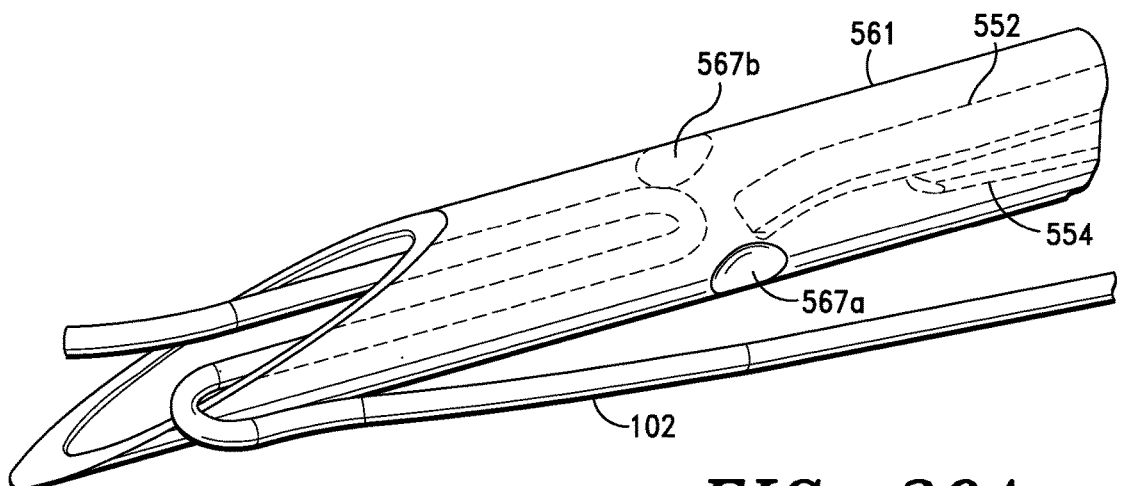
FIGS. 20A and 20B are perspective views of the cannula shaft shown in FIGS. 17B and 17C, illustrating the release of a suture from the suture capture means when the suture capture means is in a fully retracted state in the cannula shaft, according to the invention.
Figure 20B:
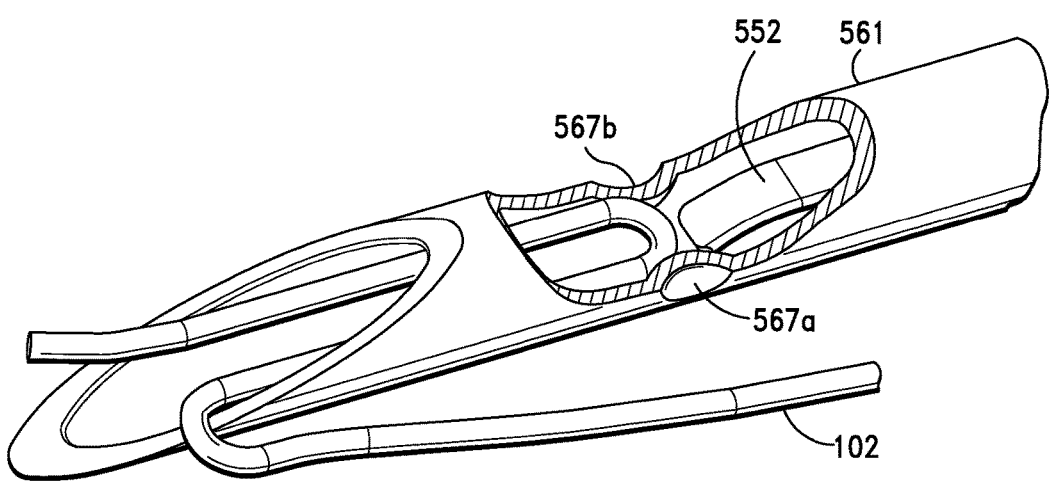

In the embodiments of the cannula shaft 561 shown in FIGS. 17B and 17C, where the cannula shaft 561 includes dimples 567a, 567b, the restricted path section or region in the cannula lumen provided by the dimples 567a, 567b, would allow the elongated top and bottom portions 552, 554 of the tong member 551 to freely traverse through the restricted path region, but would aid in the release of the suture 102 when disposed proximate the restricted region, as shown in FIGS. 20A and 20B.

According to the invention, the suture deployment shaft 540 and tubular cannula shaft 560 can comprise various conventional materials, such as polymeric materials and metal alloys. In a preferred embodiment, the suture deployment shaft 540 and tubular cannula shaft 560 comprise stainless steel.

The housing 510 and actuator 530 of the suture passer sub-system 500a can similarly comprise various conventional materials. In a preferred embodiment, the housing 510 and actuator 530 comprise a polymeric material. According to the invention, suitable polymeric materials include, without limitation, any of the aforementioned polymeric materials.

TAC System Operation

Operation of a TAC system 100 of the invention will now be described in detail.

As set forth in detail herein, the TAC systems 100 are configured to (i) pierce through biological tissue and provide access to internal structures; particularly, intra-abdominal structures, to facilitate entry through the tissue with surgical instruments and interaction of the surgical instruments with internal structures, and (ii) close an openings in the biological tissue, more preferably, approximate and/or ligate and/or fixate and close openings in biological tissue; particularly, laparoscopic ports or incisions in biological tissue. The TAC systems 100 of the invention thus preferably comprise two modes: (i) a "tissue access" mode and (ii) a "tissue closure" mode.

Figure 21:
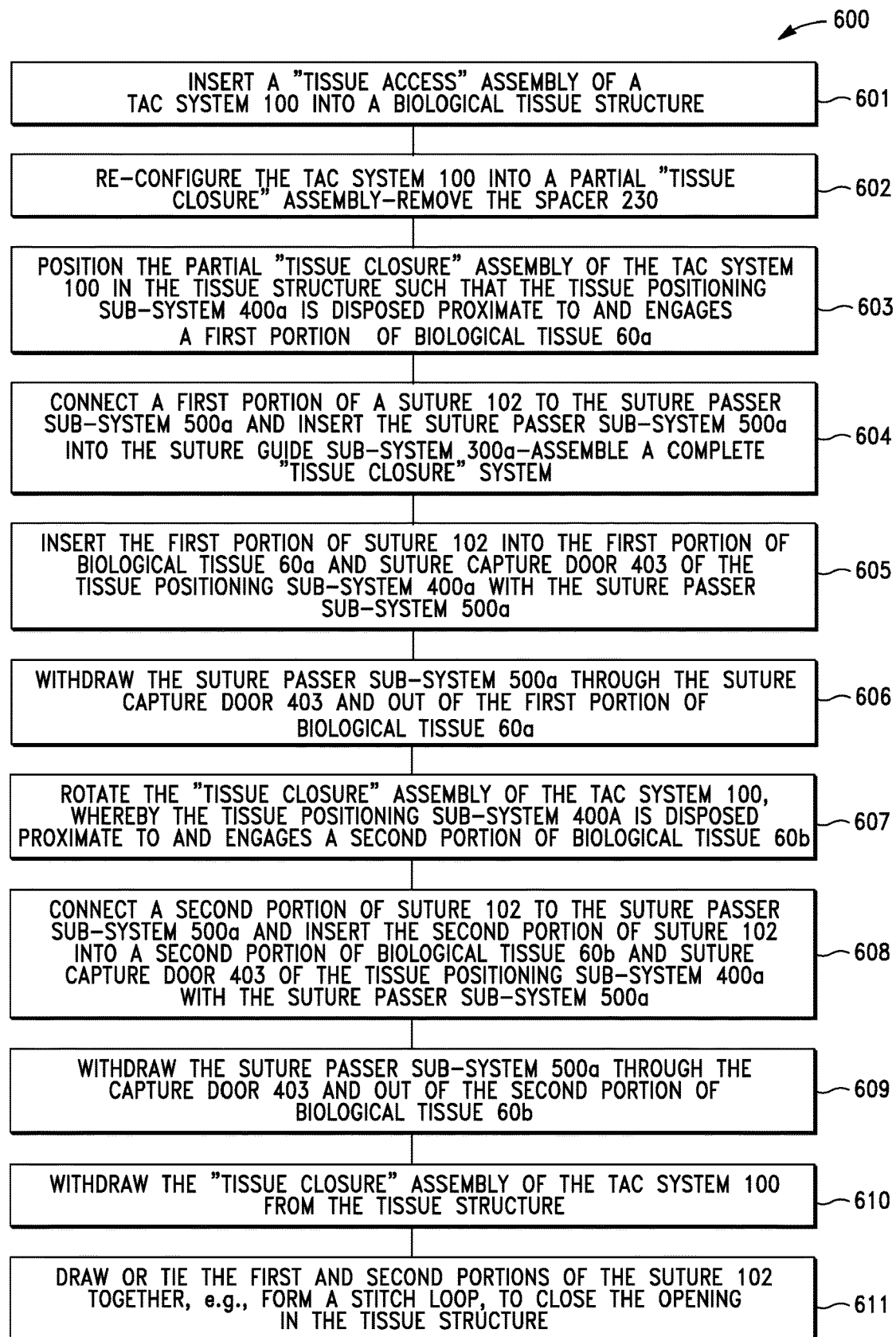
FIG. 21 is a flow chart, illustrating one embodiment of a method for accessing biological tissue and closing an opening in the tissue, according to the invention.

Referring now to FIG. 21, there is shown a flow chart illustrating a preferred method 600 of the invention for (i) piercing through biological tissue and providing access to internal structures using a "tissue access" assembly of a TAC system 100 of the invention and (ii) closing an opening in the tissue using a "tissue closure" assembly of the TAC system 100.

In the preferred method described herein, the "tissue access" assembly comprises cannula sub-system 200 and spacer 230, shown in FIGS. 5 and 6, and suture guide sub-system 300a, shown in FIG. 7A, and the "tissue closure" assembly comprises cannula sub-system 200, suture guide sub-system 300, and suture passer sub-system 500a, shown in FIG. 14.

For purposes of describing the preferred method, the tissue structure pierced and closed with the TAC system 100 comprises an abdominal tissue wall 12, comprising an adipose tissue layer 54, a muscle/fascia layer 56 and a peritoneum layer 58. The abdominal wall tissue (denoted collectively "16" herein) also comprises a top skin layer (not shown).

As stated above, the TAC systems 100 of the invention and, hence, methods employing same are not, however, limited to solely piercing and closing abdominal tissue and structures and/or surgical procedures relating thereto. Indeed, the TAC systems 100 of the invention and methods employing same can also be readily employed to pierce into and through other tissue structures (and provide access to internal structures) and close openings in other tissues and tissue structures.

As illustrated in FIG. 21, after an incision is made in the biological tissue (and, hence, tissue structure), the TAC system 100 identified above is configured in a "tissue access configuration" and inserted into (and, preferably, through) the tissue structure, i.e., the opening provided by the incision [601].

Figure 22:
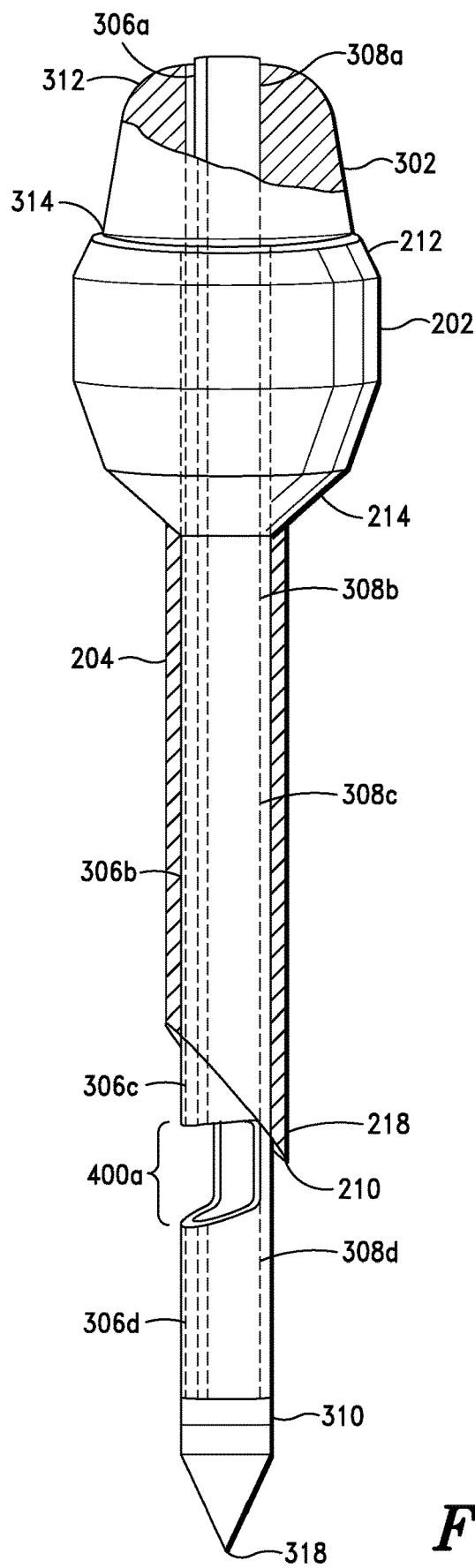
FIG. 22 is a front plan view of the assembled cannula and suture guide sub-systems shown in FIGS. 5, 6 and 7, according to the invention.

As illustrated in FIGS. 22, 23A and 23B, after the "tissue access" assembly of the TAC system 100 is inserted into the tissue structure, the TAC system 100 is re-configured into a partial "tissue closure" assembly [602], i.e., spacer 230 is removed, wherein tissue positioning sub-system 400a is exposed.

The partial "tissue closure" assembly, i.e., assembled cannula and suture guide sub-systems 200, 300a, is then positioned in an opening 11 (see FIG. 24) of a biological tissue structure such that the exposed tissue positioning sub-system 400a is disposed proximate to and engages a first portion of biological tissue 60a [603]. In the illustrated embodiment, the first portion of biological tissue 60a comprises a portion of intra-abdominal tissue, more preferably, a portion of muscle/fascia and peritoneum layers 56, 58.

In some embodiments of the invention, wherein suture guide sub-system 300a is employed and the suture guide sub-system 300a includes adjustable tissue capture means 405, after the first portion of biological tissue 60 is engaged by the tissue positioning sub-system 400a, the adjustable tissue capture means 405 is actuated, wherein the first portion of biological tissue 60a is engaged by the adjustable tissue capture means 405.

Referring back to FIG. 21, after the first portion of biological tissue 60a is engaged by the tissue positioning sub-system 400a [603], the suture passer sub-system 500 is inserted into the suture guide sub-system 300a, i.e., the tubular cannula shaft 560 of the suture passer sub-system 500a is inserted into the continuous suture lumen 306c of the suture guide sub-system 300a [604], whereby the complete "tissue closure" assembly of the TAC system 100 referenced above is formed.

A first portion of suture 102 is then connected to the suture deployment shaft (or needle) 540 of the suture passer sub-system 500a and the cannula shaft 560 with the suture deployment shaft 540 (with the first portion of suture 102 engaged thereto) disposed therein is inserted into and through the first portion of biological tissue 60a and suture capture door 403 of the tissue positioning sub-system 400a [605].

After the first portion of suture 102 is inserted into and through the first portion of biological tissue 60a and suture capture door 403 of the tissue positioning sub-system 400a with the suture passer sub-system 500a [605], the cannula shaft 560 (and, hence, suture deployment shaft 540) is withdrawn through of the suture capture door 403 and out of the first portion of biological tissue 60a [606], whereby the first portion of suture 102 is routed through the first portion of biological tissue 60a and captured or ensnared by the suture capture door 403 of the tissue positioning sub-system 400a.

As illustrated in FIGS. 23A and 23B, after the cannula shaft 560 of the suture passer sub-system 500a is withdrawn out of the first portion of biological tissue 60a [606], the suture passer sub-system 500S is further withdrawn in continuous suture lumen 306c and, preferably, out of the tissue guide sub-system 300a, and the "tissue closure" assembly of the TAC system 100 is rotated, preferably, rotated approximately 180° [607], whereby a contralateral second portion of biological tissue 60b is engaged by the tissue positioning sub-system 400a of the suture guide sub-system 300a.

Referring to FIG. 233, after the "tissue closure" assembly of the TAC system 100 is rotated [607], a second portion of suture 102 is connected to the suture deployment shaft 540 of the suture passer sub-system 5006 and the cannula shaft 60 with the suture deployment shaft 540 (with the second portion of suture 102 engaged thereto) disposed therein is inserted into and through a second portion of biological tissue 60b and past the suture capture door 403 [608].

After the second portion of suture 102 is inserted into and through the second portion of biological tissue 60b and suture capture door 403 with the suture passer sub-system 500a [608], the cannula shaft 560 is similarly withdrawn through suture capture door 403 and out of the second portion of biological tissue 60b, whereby the second portion of suture 102 is routed through the second portion of biological tissue 60b and ensnared by the suture capture door 403 of the tissue positioning sub-system 400a [609].

Both the first and second sections of suture 102 are now ensnared by the suture capture door 403 of the tissue positioning sub-system 400*a*.

Figure 24:
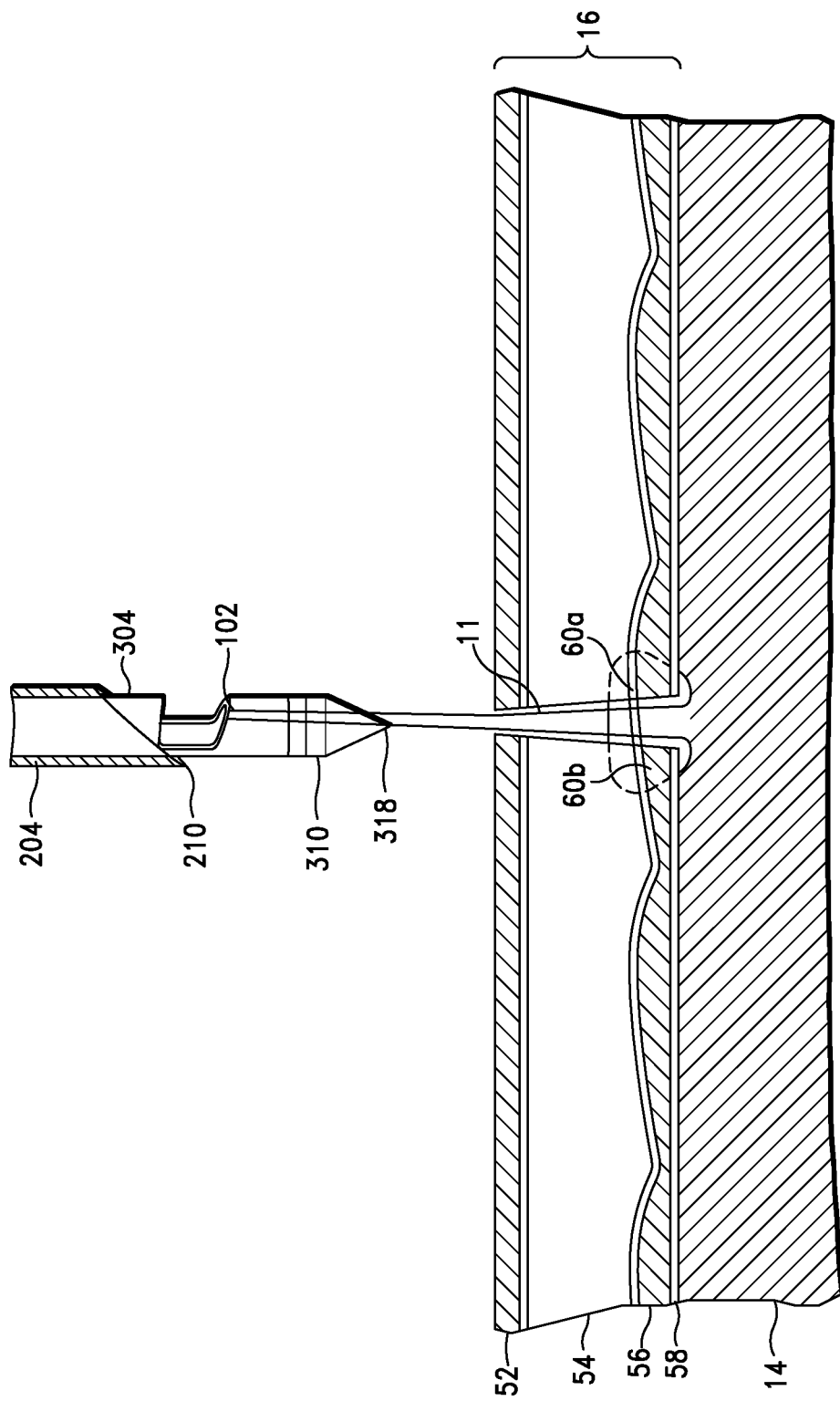
FIG. 24 is a front plan view of the assembled cannula and suture guide sub-systems shown in FIGS. 5, 6 and 7 withdrawn from biological tissue, illustrating the placement of a suture by a suture passer sub-system, according to the invention.

Referring now to FIG. 24, after the suture passer sub-system 500*a* is withdrawn out of the second portion of biological tissue 60*b* [609], the assembled cannula and suture guide sub-systems 200, 300*a* (i.e., partial "suture closure" assembly) are also withdrawn from the biological tissue structure, e.g., abdominal wall 12, with the first and second portions of suture 102 ensnared by the suture capture door system 403 of the tissue positioning sub-system 400*a* [610].

After the complete "tissue closure" assembly of the TAC system 100 is withdrawn from the biological tissue structure [610], the first and second portions of the suture 102 are released from the suture door 403 and drawn together or tied, e.g., a stitch loop is formed, whereby the first and second portions of biological tissue 60*a*, 60*b* are drawn together and the opening 11 in the tissue structure is closed, more preferably, ligated, fixated and closed [611].

According to the invention, a further tissue passer sub-system 500 that can also be employed with a TAC system 100 of the invention, i.e., a"tissue closure" assembly thereof, is disclosed in Applicant's U.S. Pat. No. 9,301,748, which is also expressly incorporated herein in its entirety.

According to the invention, the method 600 illustrated in FIG. 21 and described above can also be performed using suture guide sub-system 300*b*. The opening in the tissue structure can also be closed using suture guide sub-system 300*b* as a stand-alone tissue closure system.

As discussed in detail below, the opening in the tissue structure can also be closed using a further tissue closure system of the invention.

Alternative Tissue Closure Systems

Figure 25:
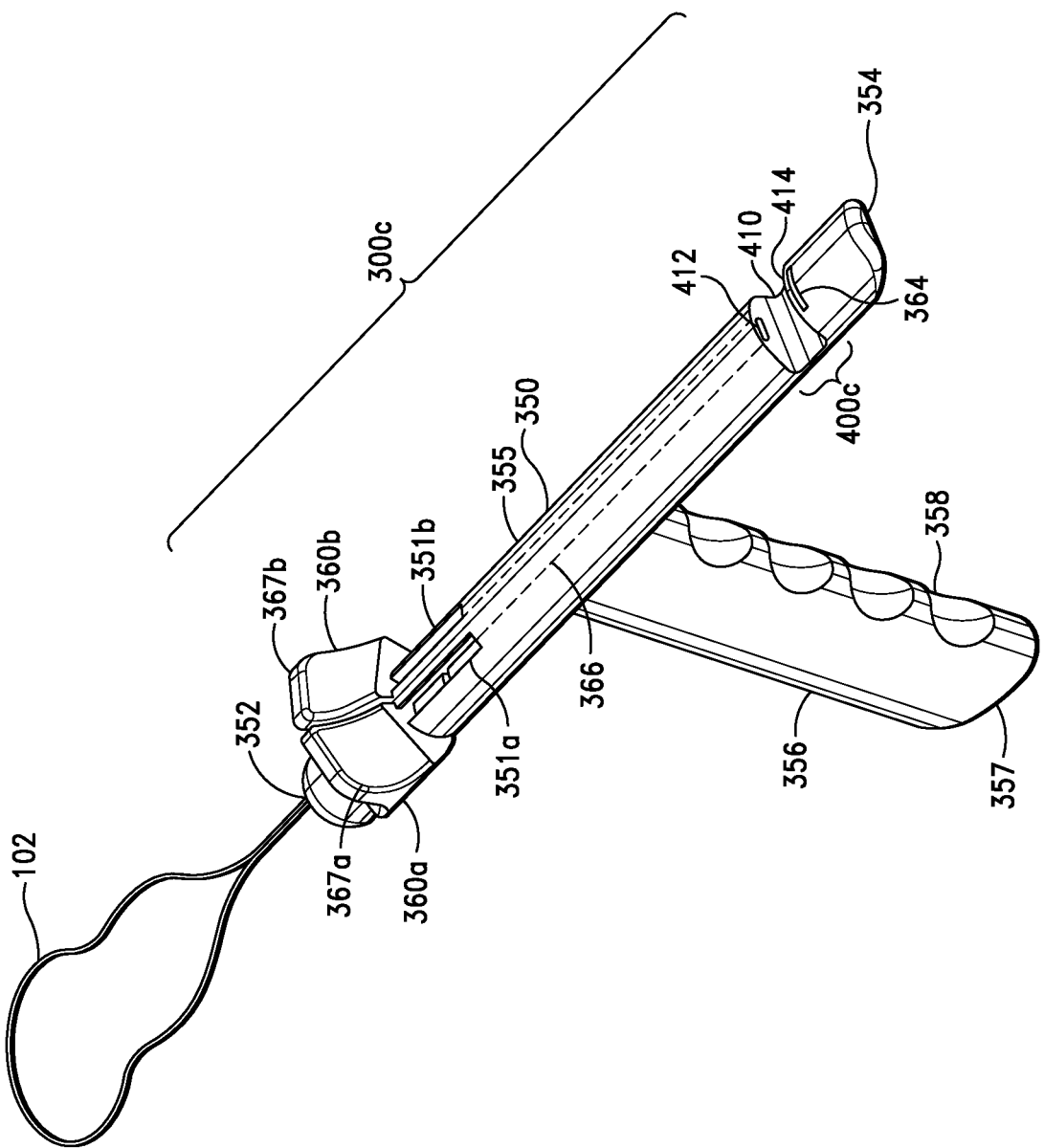
FIG. 25 is a perspective view of one embodiment of a tissue closure system, according to the invention.
Figure 26:
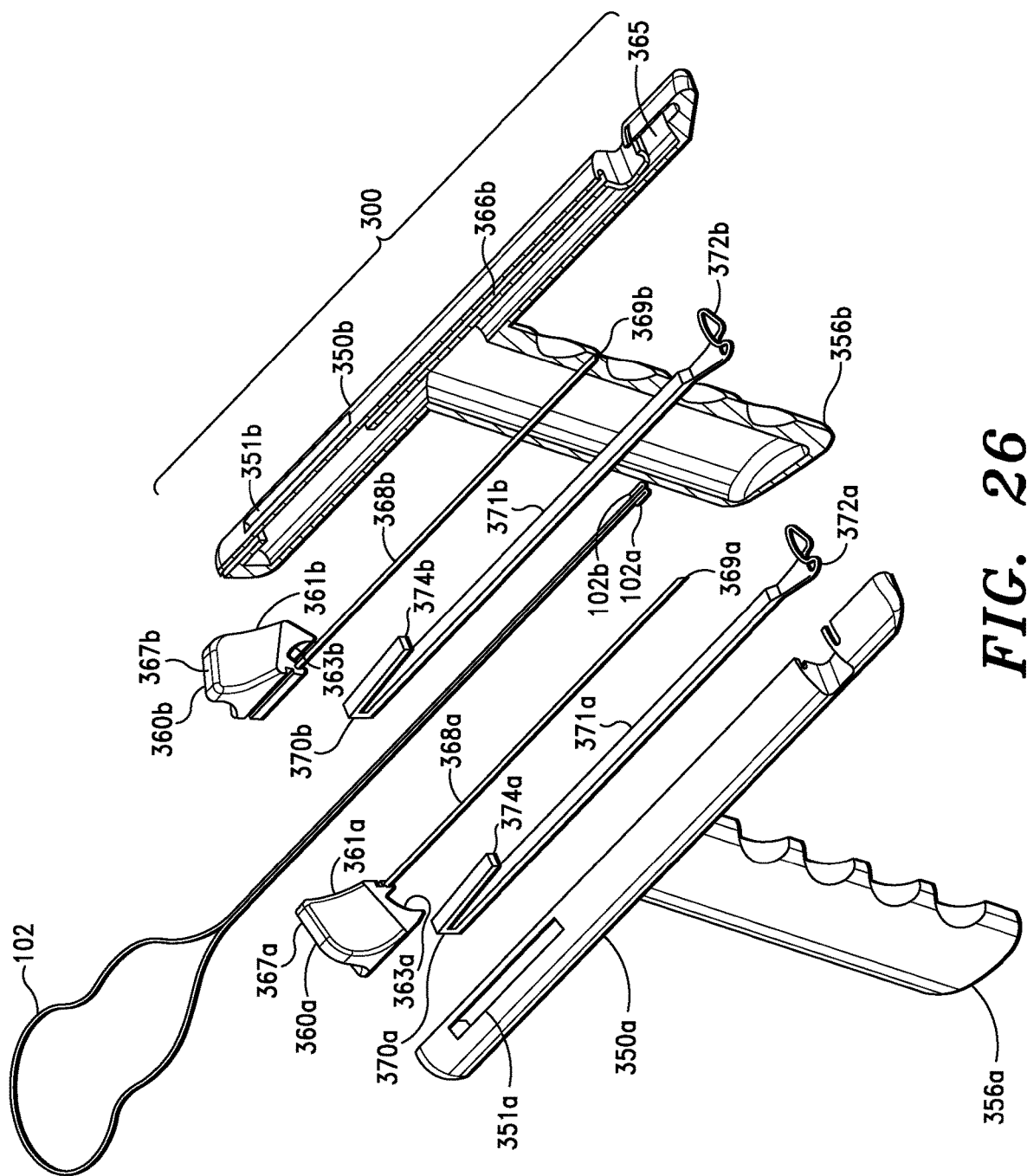
FIG. 26 is an exploded perspective view of the tissue closure system shown in FIG. 25, according to the invention.

Referring now to FIGS. 25 and 26, there is shown an alternative suture guide system 300*c* that can be employed with a TAC system 100 of the invention, i.e., a "tissue closure" assembly of a TAC system 100, or as a stand-alone suture guide and tissue closure system.

As illustrated in FIGS. 25 and 26, in a preferred embodiment of the invention, the suture guide system 300*c* comprises a housing 350, having an elongated guide region 355 with proximal and distal ends 352, 354 and a handle 356, a pair of sliders 360*a*, 360*b*, a pair of suture snares 372*a*, 372*b* and a suture 102. According to the invention, the distal end 354 of the housing elongated guide region (beyond the tissue positioning region 400*c*, discussed below) functions as a safety shield to ensure that the suture cannula shafts 368*a*, 368*b*, discussed below, do not overextend and puncture undesired tissue.

As illustrated in FIG. 26, each slider 360*a*, 360*b* includes an actuator 367*a*, 367*b* and a suture cannula shaft 368*a*, 368*b*, which is operatively connected thereto. In a preferred embodiment, the actuators 367*a*, 367*b* comprise a raised top region 361*a*, 361*b*, which is configured to facilitate operation of the actuators 367*a*, 367*b* by an operator's thumb (or other finger), and a curved bottom region 363*a*, 363*b* comprising a shape that cooperates with the outer shape of the system housing 350 (see also FIG. 25).

As further illustrated in FIG. 26, each suture snare 370*a*, 370*b* includes an elongated shaft 371*a*, 371*b*, having a flexible hooked end 374*a*, 374*b* on one end and a flexible suture capture member 372*a*, 372*b* on the opposing end.

As further illustrated in FIG. 26, the housing 350 comprises first and second housing sections 350*a*, 350*b*, i.e., a two-piece structure, which, when operatively connected, form an internal region 365 that is configured to receive and guide suture snares 370*a*, 370*b* and an internal lumen 366 that is configured to receive and guide the suture cannula shafts 368*a*, 368*b*. In a preferred embodiment, each housing section 350*a*, 350*b* comprises a guide slot 351*a*, 351*b* that is configured to receive a respective one of the flexible looped ends 374*a*, 374*b* of a suture snare 370*a*, 370*b*.

Referring back to FIG. 25, the housing 350 two-piece structure, when operatively connected, further forms a tissue positioning (or engagement) region, i.e., notch, 400*c*, which, as discussed in detail below, is similarly configured to close biological tissue, more preferably, approximate and/or ligate and/or fixate and close biological tissue; particularly, laparoscopic ports or incisions in biological tissue.

Operation of the suture guide system 300*c* will now be described in detail.

Although operation of the suture guide system 300*c* is described herein in connection with closing laparoscopic ports, the suture guide system 300*c* is not limited to merely closing laparoscopic ports. According to the invention, the suture guide system 300*c* can also be employed with or implemented in other surgical apparatus, such as a catheter or other flexible housing where flexible components of which can be used to facilitate accessing remote anatomy.

Figure 27:
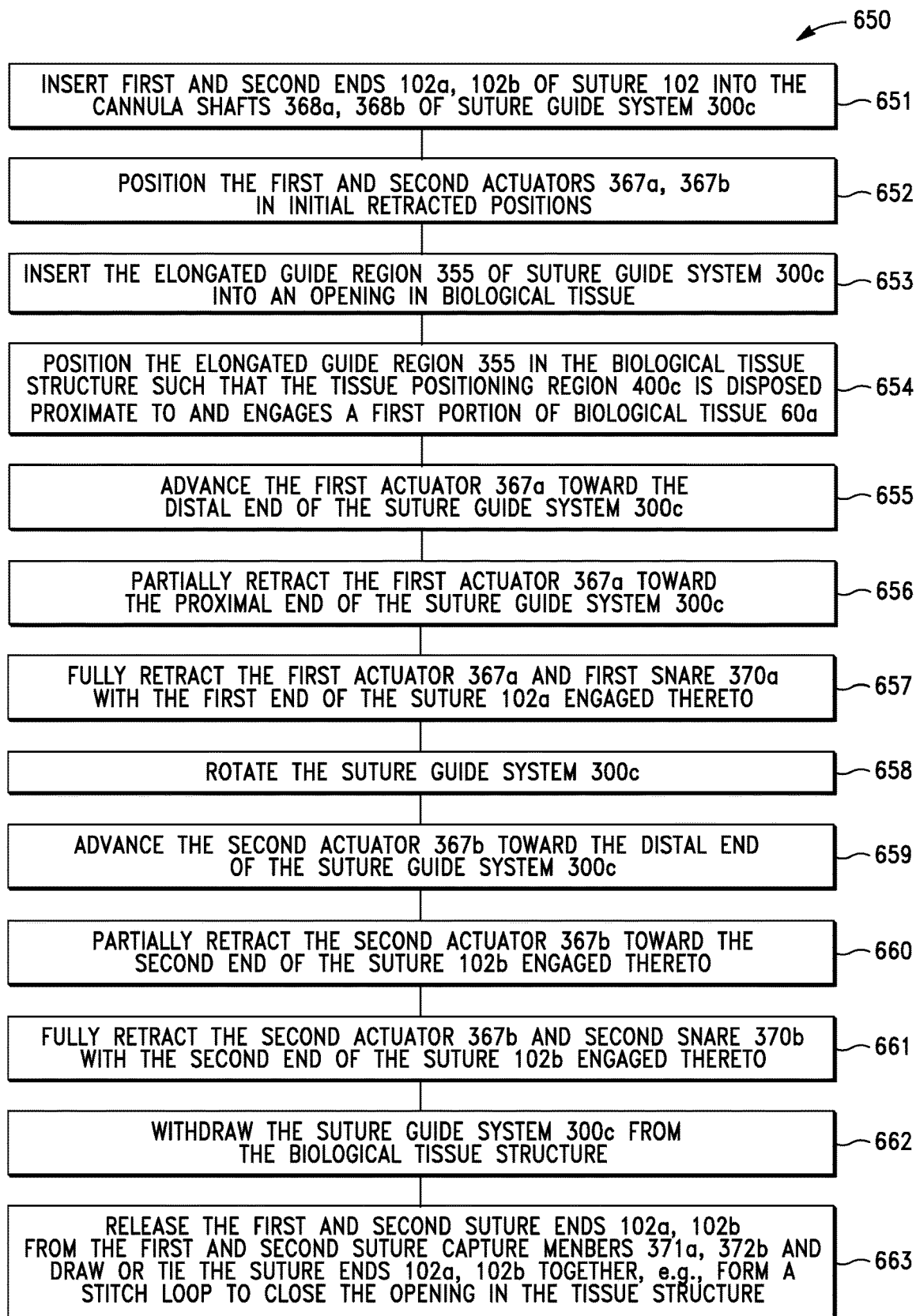
FIG. 27 is a flow chart, illustrating one embodiment of a method for closing an opening in biological tissue using the tissue closure system shown in FIG. 25, according to the invention.

Referring now to FIG. 27, there is shown a flow chart illustrating another method 650 for closing an opening in biological tissue using the suture guide system 300*c* shown in FIG. 25.

Figure 28:
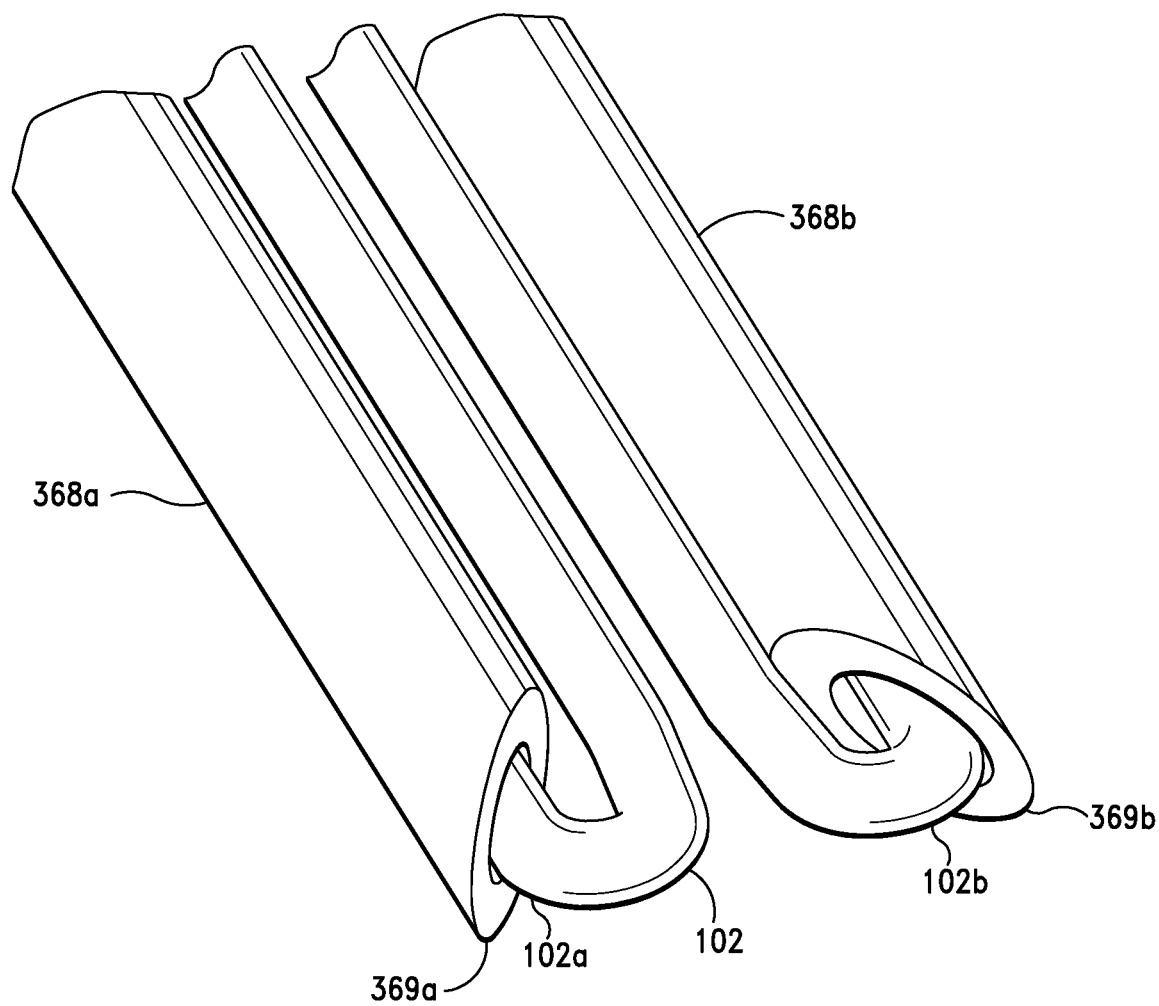
FIG. 28 is a partial perspective view of cannula shafts of the tissue closure system shown in FIG. 25 with ends of a suture operatively connected thereto, according to the invention.
Figure 30B:
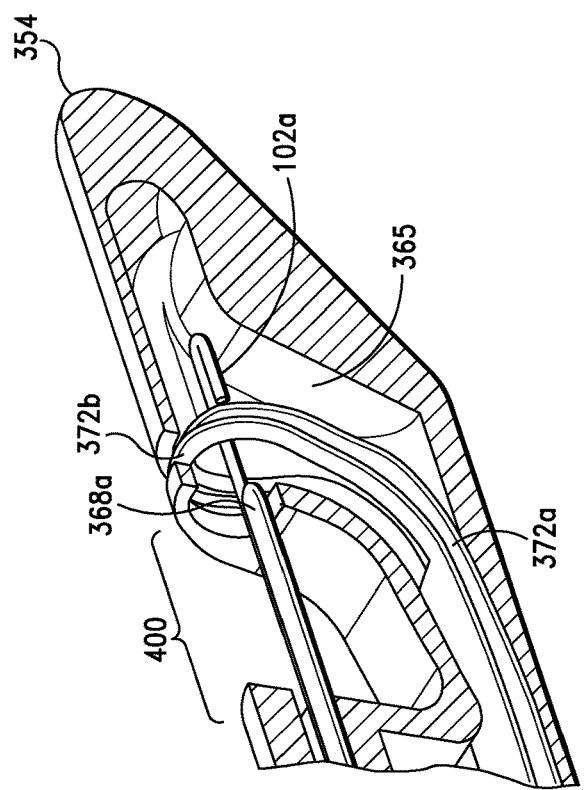
FIG. 30B is another partial perspective view of the tissue closure system shown in FIG. 25, illustrating the position of the cannula shaft in the tissue positioning region, when the actuator shown in FIG. 29A is in an advanced position, according to the invention.
Figure 30A:
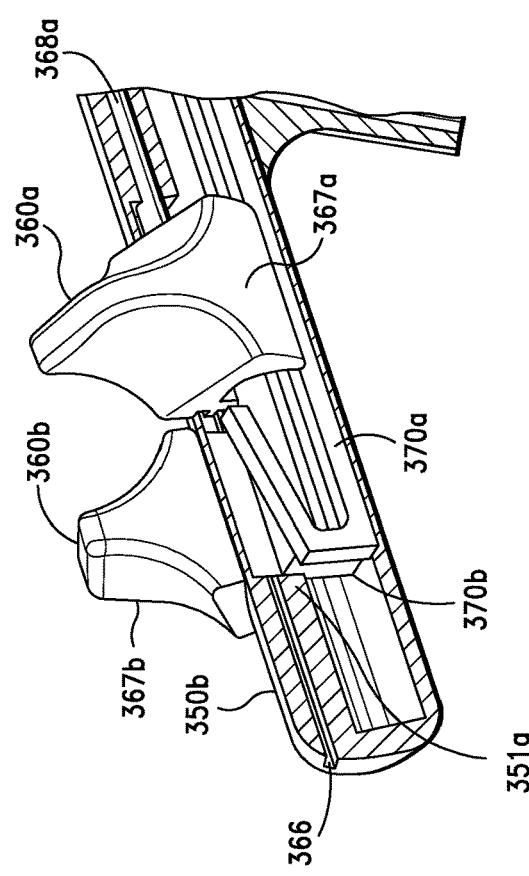
FIG. 30A is another partial perspective view of the tissue closure system shown in FIG. 25 with the actuator shown in FIG. 29A engaged to a suture snare member, according to the invention.

As set forth in the flow chart, i.e., FIG. 27, and illustrated in FIG. 28, first and second ends 102*a*, 102*b* of suture 102 are first loaded into the distal ends of 369*a*, 369*b* of cannula shafts 368*a*, 368*b*, respectively [651].

Referring now to FIG. 29A, after the first and second ends 102*a*, 102*b* of suture 102 are loaded into the distal ends of 369*a*, 369*b* of cannula shafts 368*a*, 368*b*, respectively [651], the first and second actuators 367*a*, 367*b*, i.e., sliders 360*a*, 360*b*, are positioned in initial retracted positions [652], whereby the first and second distal ends distal ends of 369*a*, 369*b* of cannula shafts 368, 368*b* are positioned proximate the tissue positioning sub-system 400*c*.

As illustrated in FIG. 29A, when the first and second actuators 367*a*, 367*b* are in an initial retracted position, the first and second flexible hooked ends 374*a*, 374*b* of the first and second suture snares 370*a*, 370*b* are deflected under the first and second actuators 367*a*, 367*b*, respectively.

Referring again to FIG. 31A, after the first and second actuators 367*a*, 367*b* are positioned in an initial retracted position [652] and an incision is made in the biological tissue (and, hence, structure), the elongated guide region 355 of suture guide system 300*c* is inserted into (and, preferably, through) the opening in the tissue structure provided by the incision [653]. In the method embodiment described herein, the biological tissue structure similarly comprises an abdominal tissue wall 12.

After the elongated guide region 355 of suture guide system 300*c* is inserted into the tissue structure [653], the elongated guide region 355 is positioned in the biological tissue structure such that the exposed tissue positioning region 400*c* is disposed proximate to and engages a first portion of biological tissue 60*a* [654]. In this instance, the first portion of biological tissue 60*a* similarly comprises a portion of intra-abdominal tissue, more preferably, a portion of muscle/fascia and peritoneum layers 56, 58.

Referring now to FIG. 29B, after the first portion of biological tissue 60*a* is engaged by the tissue positioning region 400. [654], the first actuator 367*a* is advanced along the first guide slot 351*a* toward the distal end 354 of the elongated guide region 355 of suture guide system 300*c*

[655]. According to the invention, when the first actuator 367a is advanced toward the distal end 354 of the suture guide system 300c, the first cannula shaft 368a is inserted into and through the first portion of biological tissue 60a engaged to the tissue positioning region 400c. The first flexible hooked end 374a of the first suture snare 370a is also no longer defected and transitions to an extended, relaxed state.

Referring now to FIG. 29C, after the first actuator 367a is advanced toward the distal end 354 of the elongated guide region 355 [655], the first actuator 367a is partially retracted toward the proximal end 352 of suture guide system 300c [656]. When the first actuator 367a is partially retracted, the first cannula shaft 368a is at least partially withdrawn from the first portion of biological tissue 60a and the suture 102 is engaged to and restrained by the first portion of biological tissue 60a. The first suture end 102a is also positioned within the first suture capture member 372a of the first suture snare 370a.

Figure 31B:
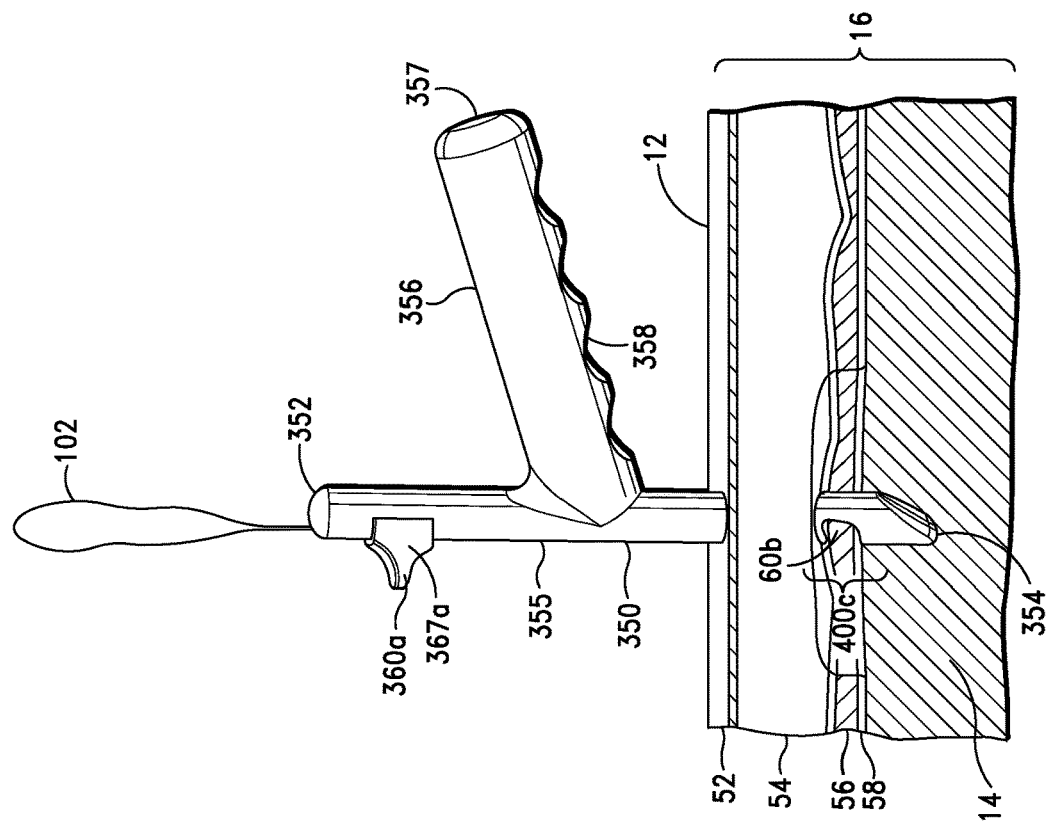
FIGS. 31A and 31B are front plan views of the tissue closure system shown in FIG. 25 positioned in a biological tissue structure, according to the invention.
Figure 31A:
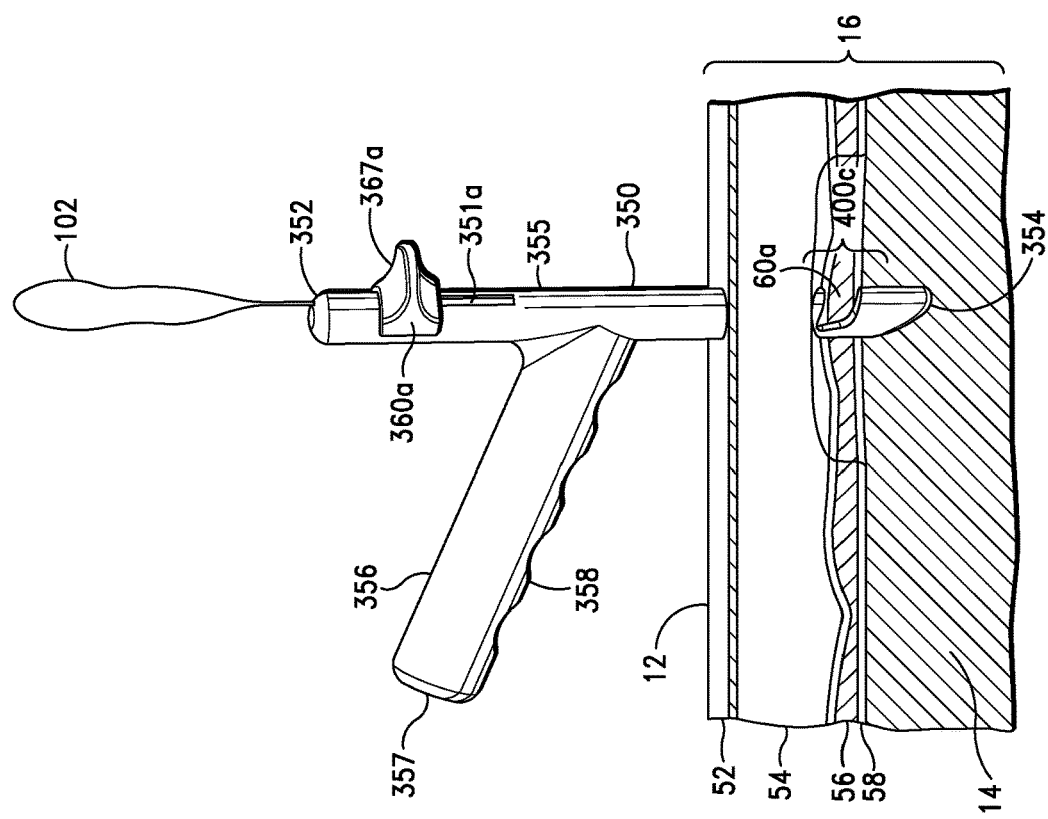

Referring now to FIG. 31A, after the first actuator 367a is partially retracted [656], the first actuator 367a is then fully retracted [657], whereby the first actuator 367a retracts the first suture snare 370a and, hence, first suture end 102a engaged thereto into the elongated guide region 355 of the suture guide housing 350.

Referring now to FIG. 31B, after the first actuator 367a is fully retracted [657], the suture guide system 300c is rotated, preferably, rotated approximately 180°, whereby a contralateral second portion of biological tissue 60b is engaged by the tissue positioning region 400c of the suture guide sub-system 300a [658].

After the suture guide system 300c is rotated [658], the second actuator 367b is advanced along the second guide slot 351b toward the distal end 354 of the elongated guide region 355 of suture guide system 300c [659]. According to the invention, when the second actuator 367b is advanced, the second cannula shaft 368b is similarly inserted into and through the second portion of biological tissue 60b engaged to the tissue positioning region 400c. The second flexible hooked end 374b of the second suture snare 370b is also no longer defected and similarly transitions to an extended, relaxed state.

The second actuator 367b is then similarly partially retracted toward the proximal end 352 of the elongated guide region 355 of suture guide system 300c [660], whereby the second cannula shaft 368b is similarly partially withdrawn from the second portion of biological tissue 60b. When the second actuator 367b is partially retracted, the second cannula shaft 368b is similarly withdrawn from the second portion of biological tissue 60b and the suture 102 is also engaged to and restrained by the second portion of biological tissue 60b. The second suture end 102b is also positioned within the second suture capture member 372b of the second suture snare 370b.

After the second actuator 367b is partially retracted [660], the second actuator 367b is then fully retracted [661], whereby the second actuator 367b similarly retracts the second suture snare 370b and, hence, second suture end 102b engaged thereto into the elongated guide region 355 of the suture guide housing 350.

After the second actuator 367b is fully retracted [661], the suture guide system 300c is withdrawn from the biological tissue structure, e.g., abdominal wall 12, with the first and second suture ends 102a, 102b ensnared by the first and second suture capture members 372a, 372b, respectively [662].

After the suture guide system 300c is withdrawn from the biological tissue structure [662], the first and second suture ends 102a, 102b are released from the first and second suture capture members 372a, 372b are tied together, whereby the opening in the tissue structure is closed, more preferably, ligated, fixated and closed [663].

In some envisioned embodiments of the invention, the suture guide system 300c further comprises a suture loading component that is adapted to load a suture into the cannula shafts 368a, 368b. In the noted embodiments, the suture 102 could run outside the housing 350 instead of within the housing 350.

According to the invention, a further alternative suture guide system that can be employed to close biological tissue is disclosed in Applicant's U.S. Pat. No. 9,393,011, which is expressly incorporated herein in its entirety.

As will readily be appreciated by one having ordinary skill in the art, the present invention provides numerous advantages compared to prior art methods and systems for accessing biological tissue (and structures) and closing openings in biological tissue. Among the advantages are the following:

The provision of tissue access and closure systems that can be readily employed to facilitate various laparoscopic surgical procedures in a simple and economical manner.

The provision of tissue access and closure systems that can be readily employed to access internal structures; particularly, intra-abdominal structures in a minimally invasive manner.

The provision of tissue access and closure systems that can be readily employed to effectively approximate, ligate, fixate and close biological tissue; particularly, laparoscopic ports or incisions in biological tissue.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A method for closing an opening in biological tissue, comprising the steps of:

providing a tissue closure system, said tissue closure system comprising a suture guide sub-system and suture passer sub-system, said suture guide sub-system comprising a proximal region, a distal region disposed opposite said proximal region, and an open internal region disposed in said distal region, said distal region being configured to transition into and through a tissue structure, said suture guide sub-system further comprising a first internal lumen that is sized and configured to receive said suture passer sub-system therein, said suture guide sub-system further comprising an open tissue positioning region disposed proximate said distal region of said suture guide sub-system, said open tissue positioning region being configured and adapted to receive tissue therein, said suture guide sub-system further comprising adjustable tissue capture means disposed proximate said open tissue positioning region, said adjustable tissue capture means being configured and positioned to linearly translate from a first position to a second position, wherein said adjustable tissue capture means is capable of engaging said tissue disposed in said open tissue positioning region of said suture guide sub-system, said suture guide sub-system further comprising a second internal lumen, said first and second internal lumens being in an aligned relationship, wherein said suture passer sub-system is capable of transitioning unobstructably from said first internal lumen into and through said open tissue positioning region and into and through said second internal lumen, said distal region of said suture guide sub-system further comprising suture retention means for controlling passage of said suture passer sub-system through said suture guide sub-system and engaging sutures releasably secured thereto, said suture retention means being disposed proximate said open tissue positioning region, said suture retention means comprising a suture capture door that is configured and positioned to obstruct passage of said suture passer sub-system through said second internal lumen of said suture guide sub-system when said suture capture door is in a closed position, said suture capture door being further configured to transition from said closed position to an open position, wherein said suture passer sub-system is allowed passage through said second internal lumen of said suture guide sub-system, said suture capture door being further configured to engage and retain a suture that is releasably secured to said suture passer sub-system when said suture passer sub-system with said suture releasably secured thereto is inserted into and through said second internal lumen of said suture guide sub-system and through said suture capture door and, thereafter, said suture passer sub-system is withdrawn through said suture capture door, whereby, when said suture passer sub-system with said suture releasably secured thereto is inserted into and through said tissue disposed in said open tissue positioning region of said suture guide sub-system, into and through said second internal lumen and through said suture capture door and, thereafter, said suture passer sub-system is withdrawn through said suture capture door, said suture is engaged to said tissue and retained by said capture door, said suture passer sub-system comprising a suture passer cannula and a suture deployment shaft, said suture passer cannula being configured to slidably receive said suture deployment shaft therein, said suture deployment shaft comprising suture deployment and capture means for delivering a first suture to biological tissue and capturing and releasably securing said first suture therewith;

inserting said suture guide sub-system into and through a tissue opening in a first biological tissue structure, said tissue opening comprising first and second tissue regions;

positioning said open tissue positioning region of said suture guide sub-system proximate said first tissue region of said first biological structure, wherein said first tissue region is disposed in said open tissue positioning region of said suture guide sub-system;

engaging a first section of said first suture with said suture passer sub-system;

inserting said suture passer sub-system and said engaged first section of said first suture into said suture guide sub-system, wherein said suture passer cannula of said suture passer sub-system is disposed proximate said first tissue region of said first biological structure;

inserting said suture passer cannula of said suture passer sub-system and said engaged first section of said first suture into and through said first tissue region of said first biological structure and through said suture capture door of said suture guide sub-system;

withdrawing said suture passer cannula through said suture capture door and out of said first tissue region of said first biological structure, wherein said first section of said first suture is ensnared by said suture capture door of said suture guide sub-system and routed through said first tissue region of said first biological structure;

withdrawing said suture passer sub-system out of said suture guide sub-system;

rotating said suture guide sub-system circumferentially, wherein said second tissue region of said first biological structure is disposed in said open tissue positioning region of said suture guide sub-system;

engaging a second section of said first suture with said suture passer sub-system;

inserting said suture passer sub-system and said engaged second section of said first suture into and through said second tissue region of said first biological structure and through said suture capture door of said suture guide sub-system;

withdrawing said first suture passer cannula through said suture capture door and out of said second tissue region of said first biological structure, wherein said second section of said first suture is ensnared by said suture capture door of said suture guide sub-system and routed through said second tissue region of said first biological structure;

withdrawing said suture passer sub-system out of said suture guide sub-system;

withdrawing said suture guide sub-system out of said first biological structure;

releasing said first and second sections of said first suture ensnared by said suture capture door; and drawing said first and second sections of said first suture together, wherein said first and second tissue regions of said first biological structure are drawn together and, thereby, said tissue opening in said first biological tissue structure is closed.

2. The method of claim 1, wherein said method further comprises the step of actuating said adjustable tissue capture means after said step of positioning said open tissue positioning region of said suture guide sub-system proximate a first tissue region of said first biological structure, wherein said first tissue region is engaged by said adjustable tissue capture means.

3. The method of claim 1, wherein said method further comprises the stop of rotating said suture guide sub-system circumferentially, wherein said contralateral second tissue region of said first biological structure is engaged by said adjustable tissue capture means.

* * * * *